United States Patent
Webber

(10) Patent No.: US 6,531,578 B1
(45) Date of Patent: Mar. 11, 2003

(54) IMMUNOASSAY METHOD EMPLOYING MONOCLONAL ANTIBODY REACTIVE TO HUMAN INOS

(76) Inventor: Robert Webber, P.O. Box 8300, Berkeley, CA (US) 94707

(*) Notice: Subject to any disclaimer, the term of this patent is extended or adjusted under 35 U.S.C. 154(b) by 0 days.

(21) Appl. No.: 08/634,332

(22) Filed: Apr. 12, 1996

(51) Int. Cl.[7] .............................................. C07K 16/00
(52) U.S. Cl. .................... 530/387.1; 530/326; 530/327; 530/328; 530/329; 530/330; 530/387.9; 530/388.26; 530/864; 435/7.2; 435/7.9; 436/518
(58) Field of Search ................................ 530/326–330, 530/387.9, 388.26, 387.1, 864; 435/7.2, 7.9–7.95, 331, 338; 436/518

(56) References Cited

U.S. PATENT DOCUMENTS

| | | | |
|---|---|---|---|
| 4,376,110 A | 3/1983 | David et al. | ................ 436/513 |
| 4,879,219 A | 11/1989 | Wands et al. | |
| 5,766,909 A | * 6/1998 | Xie et al. | ................... 435/189 |

FOREIGN PATENT DOCUMENTS

WO          23038        * 10/1994

OTHER PUBLICATIONS

Nakane et al FEBS Letters vol. 316 p. 175, Jan. 1993.*
Marsden et al Febs Letters vol. 307 p. 287, Aug. 1992.*
Scott, Trends in Biotechnology vol. 3 p. 170, 1985.*
Harlow and Lane, "Antibodies" p. 72–75, 1988.*
Volk et al, Abstract from "Immunology, Microbiology and Inflammatory Disorders", May 1995.*
Maier et al, Biochimica et Biophysica Acta vol. 1208 p. 145, Sep. 1994.*
Kobzik et al, Am. J. Respir. Cell Mol. Biol. vol. 9 p. 371, 1993.*
Ikeda, Tojo Medical Journal vol. 65 p. 433, Jun. 1995.*
"Purification and cDNA Sequence of an Inducible Nitric Oxide Synthase from a Human Tumor Cell Line", Sherman et al., Biochemistry 1993, 32, 11600–11605.
"Polyclonal Antibody Against an Inducible Form of Nitric Oxide Synthase Purified from the Liver of Rats Treated with Propionibacterium Acnes and Lipopolysaccharide", Ohshima et al.., Biochemical and Biophysical Research Communications Sep. 30, 1992, pp. 1291–1297.
"Comparison of the Sensitivity & Specificity of a Polyclonal Versus Monoclonal Capture Antibody Based Bead ELISA for Direct Detection of Cholera Toxin from Stool Specimens", Ramamurthy et al., National Library of Medicine: IGM Full Record Screen, Indian J. Med Res Jul. 1996; 104:125–8.
"Which Proliferation Markers for Routine Immunohistology? A Comparison of Five Antibodies", Rose et al., Department of Histopathology, Whittington Hospital, Highgate Hill, London, May 10, 1994. p. 1010.

"A Comparison of 13 Different Immunometric Assay Kits for Gonadotropins: Implications for Clinical Investigation", Taylor et al., Journal of Clinical Endocrinology and Metabolism, vol. 79, No. 1, 1994. p. 240.
"Glycoprotein Hormone Isomorphism and Assay Discrepancy: The Paradigm of Luteinizing Hormone (LH)", Costagliola et al., J. Endocrinol. Invest. 17: 291–299, 1994.
"European Collaborative Study on Luteinizing Hormone Assay: 2. Discrepancy Among Assay Kits is Related to Variation Both in Standard Curve Calibration and Epitope Specificity of Kit Monoclonal Antibodies", Costagliola et al., J. Endocrinol. Invest 17: 407, 1994.
"Effect of Antibodies on Chemiluminescence and on Killing of *Streptococcus Sobrinus* by Polymorphonuclear Leukocytes", Raamsdonk et al., National Liabrary of Medicine IGM Full Record Screen, Oral Microbiol Immunol Aug. 1996; 11(4):254–8.
"Immunohistochemical deminstration of a Paracrine Role of Nitric Oxide in Bronchial Function", Rengasamy et al., American Physiological Society ((1994) p. L704.
"The Molecule of the Year" by Koshland et al., Science Magazine, vol. 258, Dec. 1992 p. 1861–1865.
Increased Production of Nitric Oxide By Neutrophils and Monocytes From Cirrhotic Patients with Ascites and Hyperdynamic Circulation by Laffi et al., vol. 22 No. 6, 1995 p. 1666.
"Molecular Cloning and Expression of Inducible Nitric Oxide Synthase From Human Hapatocytes" by Geller et al., Proc. Natl. Acad. Sci, USA, vol. 90 (Apr. 1993) p. 3491.
"Increased Nitric Oxide Synthase Activity Despite Lack of Response To Endothelium–Dependent Vasodilators in Postischemic Acute Renal Failure in Rats", by Conger et al., The Journal of Clinical Investigations, Inc., vol. 96 (Jul. 1995) p. 631.
"Immunohistochemistry in the Identification of Nitric Oxide Synthase Isoenzymes in Myocardial Infarction", by Wildhirt et al., Cardiovascular Research, vol. 29 (1995) p. 526.
"The Nitric Oxide Synthase Family of Proteins" by Sessa, W., J. Vasc, Res. (1994) p. 131–143.
"Expression and Preferential Inhibition of Inducible Nitric Oxide Synthase in Aortas of Endotoxemic Rats" by Weigert et al., Journal of the American Society of Nephrology, vol. 5, No. 12 (1995) p. 2067.
"Stabilization of Inducible Nitric Oxide Synthase by Monoclonal Antibodies" by Hattori et al., Hybridoma, vol. 12, No. 6 (1993) p. 763.

(List continued on next page.)

Primary Examiner—Sheela Huff
(74) Attorney, Agent, or Firm—Theodore J. Bielen, Jr.

(57) ABSTRACT

A panel of monoclonal antibodies recognizing and binding to human inducible nitric oxide synthase (iNOS or type II iNOS) enzyme have been developed. The monoclonal antibodies may also be employed in an assay to detect the presence and/or quantitate the amount of human iNOS.

9 Claims, 20 Drawing Sheets

OTHER PUBLICATIONS

"Transient Expression of Calcium–INdependent Nitric Oxide Synthase in Blood Vessels During Brain Development" by Galea et al., FASEB Journal, vol. 9, Dec. 1995 p. 1632.

"Inducible Nitric Oxide Synthase In A Human Glioblastoma Cell Line" by Fujisawa et al. Journal of Neurochemistry, vol. 64 (1995) p. 85.

"Immunochemical Detection of Inducible NO Synthase in Human Lung" by Tracey et al., American Physiological Society, Rapid Communication (1994) p. L722.

"Characterization and Localization of Endothelial Nitric Oxide Synthase Using Specific Monoclonal Antibodies" by Pollock et al., American Physiological Society (93) 1993 p. C1 379.

Brochure from Transduction Laboratories, Lexington, Kentucky, (1995) Cat. NOS. N 31030 N 31020, N 30030, and N 32024, N 32030, N 32020, N 30020.

Brochure, "Signaling Intermediates—NOS" Santa Cruz Biotechnology p. 208 (1995).

Brochure, "Isostrip" by Boehringer Manneheim Corporation, Catalog No. 1493–027 (1995).

"Basic Local Alignment Search Tool" by Altschul et al., J. Mol. Biol. (1990) p. 403–410.

"Production of Monoclonal Antibodies" by Current Protocols in Immunology (1991).

"Macrophage Deactivating FActor and Transforming Growth Factors Beta1, Beta2, Beta3, Inhibit Induction of Macrophage Nitrogen Oxide Synthesis by IFN–Y1" by Ding et al. The Journal of Immunology (1990) p. 940.

"Cloned Human Brain Nitric Oxide Synthase is Highly Expressed in Skeletal Muscle" by Nakane et al., Federation of European Biochemical Societies, Jan. 1993 p. 175–180.

* cited by examiner

FIG. 1

Seq. 1:

| Gly | Ile | Val | Pro | Phe | Arg | Ser | Phe | Trp | Gln | Gln | Arg | Leu |
|-----|-----|-----|-----|-----|-----|-----|-----|-----|-----|-----|-----|-----|
|     |     |     |     | 5   |     |     |     |     | 10  |     |     |     |
| His | Asp | Ser | Gln | His |     |     |     |     |     |     |     |     |
|     | 15  |     |     |     |     |     |     |     |     |     |     |     |

Seq. 2:

| Pro | Ala | Leu | Val | Gln | Gly | Ile | Leu | Glu | Arg | Val | Val | Asp |
|-----|-----|-----|-----|-----|-----|-----|-----|-----|-----|-----|-----|-----|
|     |     |     |     | 5   |     |     |     |     | 10  |     |     |     |
| Gly | Pro | Thr | Pro | His |     |     |     |     |     |     |     |     |
|     | 15  |     |     |     |     |     |     |     |     |     |     |     |

Seq. 3:

| Asn | Asn | Asn | Val | Glu | Lys | Ala | Pro | Ser | Ala | Thr | Ser | Ser |
|-----|-----|-----|-----|-----|-----|-----|-----|-----|-----|-----|-----|-----|
|     |     |     |     | 5   |     |     |     |     | 10  |     |     |     |
| Pro | Val | Thr | Gln | Asp |     |     |     |     |     |     |     |     |
|     | 15  |     |     |     |     |     |     |     |     |     |     |     |

Seq. 4:

| Ser | Pro | Val | Thr | Gln | Asp | Asp | Leu | Gln | Tyr | His | Asn | Leu |
|-----|-----|-----|-----|-----|-----|-----|-----|-----|-----|-----|-----|-----|
|     |     |     |     | 5   |     |     |     |     | 10  |     |     |     |
| Ser | Lys | Gln | Gln | Asn |     |     |     |     |     |     |     |     |
|     | 15  |     |     |     |     |     |     |     |     |     |     |     |

Seq 5:

| Arg | Met | Thr | Leu | Val | Phe | Gly | Ser | Arg | Arg | Pro | Asp | Glu |
|-----|-----|-----|-----|-----|-----|-----|-----|-----|-----|-----|-----|-----|
|     |     |     |     | 5   |     |     |     |     | 10  |     |     |     |
| Asp | His | Ile | Tyr | Gln |     |     |     |     |     |     |     |     |
|     | 15  |     |     |     |     |     |     |     |     |     |     |     |

FIG. 7

Seq. 6:

Asn  Asn  Asn  Val  Glu  Lys  Ala  Pro  Ser  Ala  Thr  Ser  Ser
                         5                        10
Pro  Val  Thr  Gln  Asp
     15

Seq. 7:

Val  Glu  Lys  Ala  Pro  Ser  Ala  Thr  Ser  Ser  Pro  Val  Thr
                         5                        10
Gln  Asp
     15

Seq. 8:

Ala  Pro  Ser  Ala  Thr  Ser  Ser  Pro  Val  Thr  Gln  Asp
                    5                   10

Seq. 9:

Ala  Thr  Ser  Ser  Pro  Val  Thr  Gln  Asp
                    5

Seq. 10:

Ser  Pro  Val  Thr  Gln  Asp
                    5

Seq. 11:

Asn  Asn  Asn  Val  Glu  Lys  Ala  Pro  Ser  Ala  Thr  Ser  Ser
                         5                        10
Pro  Val
     15

Seq. 12:

Asn  Asn  Asn  Val  Glu  Lys  Ala  Pro  Ser  Ala  Thr  Ser
                         5                        10

Seq. 13:

Asn  Asn  Asn  Val  Glu  Lys  Ala  Pro  Ser
                         5

Seq. 14:

Asn  Asn  Asn  Val  Glu  Lys
                         5

FIG. 7A

Seq. 15:

Ser Pro Val Thr Gln Asp Asp Leu Gln Tyr His Asn Leu
                    5                   10
Ser Lys Gln Gln Asn
    15

Seq. 16:

Thr Gln Asp Asp Leu Gln Tyr His Asn Leu Ser Lys Gln
                5                   10
Gln Asn
    15

Seq. 17:

Asp Leu Gln Tyr His Asn Leu Ser Lys Gln Gln Asn
            5                   10

Seq. 18:

Tyr His Asn Leu Ser Lys Gln Gln Asn
                5

Seq. 19:

Leu Ser Lys Gln Gln Asn
                5

Seq. 20:

Ser Pro Val Thr Gln Asp Asp Leu Gln Tyr His Asn Leu
                    5                   10
Ser Lys
    15

Seq. 21:

Ser Pro Val Thr Gln Asp Asp Leu Gln Tyr His Asn
                    5                   10

Seq. 22:

Ser Pro Val Thr Gln Asp Asp Leu Gln
                    5

Seq. 23:

Ser Pro Val Thr Gln Asp
                    5

FIG. 7B

Seq. 24:

Pro Ala Leu Val Gln Gly Ile Leu Glu Arg Val Val Asp
                    5                   10
Gly Pro Thr Pro HIs
15

Seq. 25:

Val Gln Gly Ile Leu Glu Arg Val Val Asp Gly Pro Thr
                5                    10
Pro His
15

Seq. 26:

Ile Lue Glu Arg Val Val Asp Gly Pro Thr Pro His
                5                   10

Seq. 27:

Arg Val Val Asp Gly Pro Thr Pro His
                5

Seq. 28:

Asp Gly Pro Thr Pro His
                5

Seq. 29:

Pro Ala Leu Val Gln Gly Ile Leu Glu Arg Val Val Asp
                    5                   10
Gly

Seq. 30:

Pro Ala Leu Val Gln Gly Ile Leu Glu Arg Val Val
                    5                   10

Seq. 31:

Pro Ala Leu Val Gln Gly Ile Leu Glu
                    5

Seq. 32:

Pro Ala Leu Val Gln Gly
                    5

Seq. 33:

Gly Ile Val Pro Phe Arg Ser Phe Trp Gln Gln Arg Leu
                    5                    10
His Asp Ser Gln His
15

FIG. 7C

Seq. 34:

| Pro | Phe | Arg | Ser | Phe | Trp | Gln | Gln | Arg | Leu | His | Asp | Ser |
|-----|-----|-----|-----|-----|-----|-----|-----|-----|-----|-----|-----|-----|
|     |     |     |     | 5   |     |     |     |     | 10  |     |     |     |
| Gln | His |     |     |     |     |     |     |     |     |     |     |     |
|     | 15  |     |     |     |     |     |     |     |     |     |     |     |

Seq. 35:

Ser Phe Trp Gln Gln Arg Leu His Asp Ser Gln His
                    5                    10

Seq. 36:

Gln Gln Arg Leu His Asp Ser Gln His
                5

Seq. 37:

His Asp Ser Gln His
                5

Seq. 38:

Gly Ile Val Pro Phe Arg Ser Phe Trp Gln Gln Arg Leu
                5                    10
His Asp
    15

Seq. 39:

Gly Ile Val Pro Phe Arg Ser Phe Trp Gln Gln Arg
                5                    10

Seq. 40:

Gly Ile Val Pro Phe Arg Ser Phe Trp
                5

Seq. 41:

Gly Ile Val Pro Phe Arg
                5

Seq. 42:

Arg Met Thr Leu Val Phe Gly Ser Arg Arg Pro Asp Glu
                5                    10
Asp His Ile Tyr Gln
    15

FIG. 7D

Seq. 43:

| Leu | Val | Phe | Gly | Ser | Arg | Arg | Pro | Asp | Glu | Asp | His | Ile |
|-----|-----|-----|-----|-----|-----|-----|-----|-----|-----|-----|-----|-----|
|     |     |     |     | 5   |     |     |     |     | 10  |     |     |     |
| Tyr | Gln |
|     | 15  |

Seq. 44:

| Gly | Ser | Arg | Arg | Pro | Asp | Glu | Asp | His | Ile | Tyr | Gln |
|-----|-----|-----|-----|-----|-----|-----|-----|-----|-----|-----|-----|
|     |     |     |     | 5   |     |     |     |     | 10  |     |     |

Seq. 45:

| Arg | Pro | Asp | Glu | Asp | His | Ile | Tyr | Gln |
|-----|-----|-----|-----|-----|-----|-----|-----|-----|
|     |     |     |     | 5   |     |     |     |     |

Seq. 46:

| Glu | Asp | His | Ile | Tyr | Gln |
|-----|-----|-----|-----|-----|-----|
|     |     |     |     | 5   |     |

FIG. 8

Seq. 47:

| Asn | Asn | Asn | Val | Lys | Lys | Thr | Pro | Ser | Ala | Val | Leu | Ser |
|-----|-----|-----|-----|-----|-----|-----|-----|-----|-----|-----|-----|-----|
|     |     |     |     | 5   |     |     |     |     | 10  |     |     |     |
| Pro | Thr | Ile | Gln | Asp |
|     | 15  |

Seq. 48:

| Asn | Asn | Asn | Val | Glu | Lys | Thr | Pro | Gly | Ala | Ile | Pro | Ser |
|-----|-----|-----|-----|-----|-----|-----|-----|-----|-----|-----|-----|-----|
|     |     |     |     | 5   |     |     |     |     | 10  |     |     |     |
| Pro | Thr | Thr | Gln | Asp |
|     | 15  |

Seq. 49:

| Pro | Gly | Leu | Val | Glu | Ala | Leu | Leu | Ser | Arg | Val | Glu | Asp |
|-----|-----|-----|-----|-----|-----|-----|-----|-----|-----|-----|-----|-----|
|     |     |     |     | 5   |     |     |     |     | 10  |     |     |     |
| Pro | Pro | Ala | Pro | Thr | Glu |
|     | 15  |

Seq. 50:

| Gly | Ile | Ala | Pro | Phe | Arg | Ser | Phe | Tyr | Gln | Gln | Arg | Gln |
|-----|-----|-----|-----|-----|-----|-----|-----|-----|-----|-----|-----|-----|
|     |     |     |     | 5   |     |     |     |     | 10  |     |     |     |
| Phe | Asp | Ile | Gln | His |
|     | 15  |

FIG. 8A

Seq. 51:

Gly Ile Ala Pro Phe Arg Gly Phe Trp Gln Glu Arg Leu
              5                        10
His Asp
    15

Seq. 52:

Met Thr Leu Val Phe Gly Ser Arg Ser Ser Gln Leu Asp
              5                        10
His Leu Tyr Arg
    15

Seq. 53:

Met Val Leu Val Phe Gly Ser Arg Gln Ser Lys Ile Asp
              5                        10
His Ile Tyr Arg
    15

IMMUNOASSAY METHOD EMPLOYING MONOCLONAL ANTIBODY REACTIVE TO HUMAN INOS

BACKGROUND OF THE INVENTION

The present invention relates to a novel and useful panel of monoclonal antibodies which may be employed in immunoassays and other procedures for detection and/or quantitation of human iNOS.

Nitric oxide (NO) has recently been recognized as an effector and/or regulator molecule. For example, a recent field of investigation focused on the activity of NO upon the activation of soluble guanylate cyclase, which is responsible for endothelial dependent relaxation in the vasculature. An article entitled "Immunohistochemical Demonstration of a Paracrine Role of Nitric Oxide in Bronchial Function" by Rangassmy et al., er gan Physiological Society (1994) recognizes this effect with respect to bronchial blood vessels.

Concurrently, investigators have discovered that NO acts as a new neurotransmitter in the central and peripheral nervous system. In addition, activated macrophage cytotoxicity was found to be activated in host defense mechanisms based on the presence of NO. NO is now considered the smallest biosynthetically derived effector molecule secreted in mammalian systems. Reference is made to an article entitled "The Molecule of the Year", Science Magazine, Volume 258 (December 1992), by Koshland, which elaborates on the physiological importance of NO.

An article entitled "Increased Production of Nitric Oxide By Neutrophils and Monocytes From Cirrhotic Patients With Ascites and Hyperdynamic Circulation", by Laffi et. al., Hepatology, Volume 22, No. 6, (1995) and an article entitled "Molecular Cloning and Expression of Inducible Nitric Oxide Synthase from Human Hepatocytes" by Geller et al., Proc. Natl. Acad. Sci. USA, Volume 90 (April 1993) describes activity of nitric oxide synthase (NOS) and of nitric oxide in the liver. The latter reference includes an amino acid sequence describing human inducible NOS. In general, these articles associate cirrhosis with its concomitant activation of hepatocytes due to the inflammation and destruction of the liver, with the induction of iNOS and the subsequent overproduction of NO.

Rejection of transplanted organs is proposed to be mediated by host defense mechanisms in which activated monocytes, macrophages, and/or neutrophils are active, and through the actions of iNOS leads to the inevitable production of NO. Others have attempted to develop drugs which specifically inhibit iNOS, thus stopping the production of NO, without simultaneously inhibiting either neuronal NOS (nNOS) or endothelial (eNOS), the other two isofroms of this enzyme.

An article entitled "Increased Nitric Oxide Synthase Activity Despite Lack of Response to Endothelium-dependent Vasodilators in Postischemic Acute Renal Failure in Rats", by Conger et al., The Journal of Clinical Investigations, Inc., Volume 96 (July 1995) recognizes nitric oxide activity in the failure of rat kidneys.

An article entitled "Immunohistochemistry in the Identification of Nitric Oxide Synthase Isoenzymes in Myocardial Infarction", by Wildhirt et al., Cardiovascular Research, Volume 29 (1995) recognizes the conversion of L-arginine to citrulline and nitric oxide in infarcted rabbit myocardium, which leads to damage of the heart.

The NO biosynthetic pathway has been extensively examined recently. It is now recognized that there is a family of isozymes which produce NO. An article entitled "The Nitric Oxide Synthase Family of Proteins", by Sessa, J. Vasc. Res. (1994) recognizes the trio of NOS isozymes. All three NOS isozymes catalyze the conversion of L-arginine and oxygen to citrulline and NO. In addition, five co-factors have also been found to be required for this catalytic conversion. These are calmodulin, NADPH, FAD, FMN, and tetrahydrobiopterin. Generally, the three isoforms of NO synthase (NOS) have been labeled type 1 (nNOS), the neuronal isoform; type 2 (iNOS), the inducible isoform; and type 3 (eNOS), the endothelial isoform. NNOS and eNOS are constitutively expressed in the cells in which they are found. iNOS is not constitutively expressed, but rather is induced by a number of cytokines and lypopolysaccarides (LPS). It has been further discovered that nNOS serves as a neurotransmitter. iNOS, further, concerns host defense and cellular immunity. Also, vascular tone and hemodynamic control has been linked to eNOS. The three (3) isoforms of the NOS enzyme fall in the category of true isozymes since they share approximately 60% sequence homology.

iNOS has been specifically implicated in certain pathological diseased states. An article entitled "Expression and Preferential Inhibition of Inducible Nitric Oxide Synthase in Aortas of Endotoxemic Rats", by Weigert et al., Journal of the American Society of Nephrology, Volume 5, No. 12 (1995) discusses the functional importance of iNOS with respect to septic shock. Specifically, where sepsis and septic shock occurs, numerous cytokines and LPS from gram negative bacteria potentially can induce the expression of iNOS in monocytes, macrophages, neutrophils, hepatocytes, or other cell types, which leads to the overproduction of NO. This in turn leads to the deleterious effects associated with sepsis and septic shock due to extensive systemic vasodilation.

Various groups of researchers have reported on the development of monoclonal antibodies to NOS and on the utilization of such antibodies for biomedical experimentation. An article entitled "Stabilization of Inducible Nitric Oxide Synthase by Monoclonal Antibodies" by Hattori et al., Hybridoma, Volume 12, No. 6 (1993) states that a panel of monoclonal antibodies to rat iNOS was derived from activated rat peritoneal macrophages. It was reported therein that none of the monoclonal antibodies neutralized the enzymatic activity of rat iNOS, but some of the monoclonal antibodies stabilized the enzyme.

An article entitled "Transient Expression of Calcium-Independent Nitric Oxide Synthase in Blood Vessels During Brain Development" by Galea et al., FASEB Journal, Volume 9, (December 1995), describes a protein band which was detected with a monoclonal antibody raised against rat iNOS. Moreover, the Rengasamy article, prior identified, describes the development and characterization of a monoclonal antibody developed to bovine nNOS. Through western immunoblots, this monoclonal antibody was found to recognize bovine nNOS, bovine eNOS, and mouse iNOS. The same monoclonal antibody was found to recognize rat nNOS, rat eNOS, and rat iNOS, by immunohistochemical techniques.

An article entitled "Inducible Nitric Oxide Synthase In A Human Glioblastoma Cell Line" by Fujisawa et al., Journal of Neurochemistry, Vol. 64 (1995) describes iNOS induction in A-172 cells, which is a human glioblastoma cell line.

An article entitled "Immunochemical Detection of Inducible NO Synthase in Human Lung" by Tracey et al., American Physiological Society, Rapid Communication (1994) describes iNOS induction in RAW 264.7 macrophages.

Polyclonal antibodies raised against mouse iNOS derived from induced RAW 264.7 cells and were used to investigate the expression of iNOS in human lung tissue.

An article entitled "Characterization and Localization of Endothelial Nitric Oxide Synthase Using Specific Monoclonal Antibodies" by Pollock et al., American Physiological Society (1993) describes the development and characterization of a panel of monoclonal antibodies developed to bovine eNOS, which do not cross react with either nNOS or iNOS.

U.S. Pat. Nos. 4,376,110 and 4,879,219 describe immunoassays utilizing monoclonal antibodies to detect antigenic substances.

A brochure from Transduction Laboratories, Lexington, Ky., offers a number of mouse monoclonal antibodies raised to recombinant fragments of various rat isoforms of NOS.

A company called Santa Cruz Biotechnology in a brochure entitled "Signaling Intermediates—NOS" offers a number of polyclonal anti-peptide antibodies specific for the various isoforms of NOS.

A brochure entitled "Isostrip" by Boehringer Mannheim Corporation illustrates a simplified mouse monoclonal antibody isotyping kit which uses treated strips to detect mouse immunoglobulin subclasses, and kappa or lambda light chains.

The development of a panel of monoclonal antibodies to human iNOS for immunoassays specific for human iNOS would be a notable advance in the bio-medical field.

SUMMARY OF THE INVENTION

In accordance with the present invention a novel and useful panel of monoclonal antibodies specific to human iNOS have been developed and have been demonstrated to be useful in immunoassays that are specific for human iNOS.

The monoclonal antibodies have been characterized by a number of different standard techniques.

An object of the present invention is the development of immunoassays which can be used as clinical tests for hiNOS utilizing monoclonal antibodies specific to hiNOS.

Another object of the present invention is to develop a separate panel of polyclonal rabbit anti-peptide antibodies, which are specific for the three (3) isoforms of hNOS.

Yet another object of the present invention is to produce peptide sequences which mimic regions of hiNOS, and that bind to the monoclonal antibodies of the present invention.

A further object of the present invention is to provide truncated peptide sequences which mimic regions of hiNOS and that bind to the monoclonal antibodies of the present invention.

Another object of the present invention is to provide homolog peptides from proteins other than human iNOS to test the specificity characteristics of the monoclonal antibodies.

Yet another object of the present invention is to characterize the panel of monoclonal antibodies of the present invention to ascertain their individual utility in various assays and procedures.

The invention possesses other objects and advantages especially as concerns particular characteristics and features thereof which will become apparent as the specification continues.

BRIEF DESCRIPTION OF THE DRAWINGS

FIG. 1 is a listing of five amino acid sequences (SEQ ID No. 24, 27–29 and 31 respectively) representing regions of hiNOS to which various monoclonal antibodies, from the overall panel of monoclonal antibodies, of the present invention have bound.

FIGS. 7A–D are a listing of the peptide sequences (SEQ ID No. 35–42, 44–51, 54–61, and 76–83 respectively) usable for epitope mapping of the monoclonal antibodies of the present invention.

FIG. 8 is a listing of the peptide sequences (SEQ ID No. 28, 34, 53, 63, 64, 74 and 75 respectively) usable to determine specificity characterization of the monoclonal antibodies of the present invention.

DESCRIPTION OF THE PREFERRED EMBODIMENTS

Figure 2:
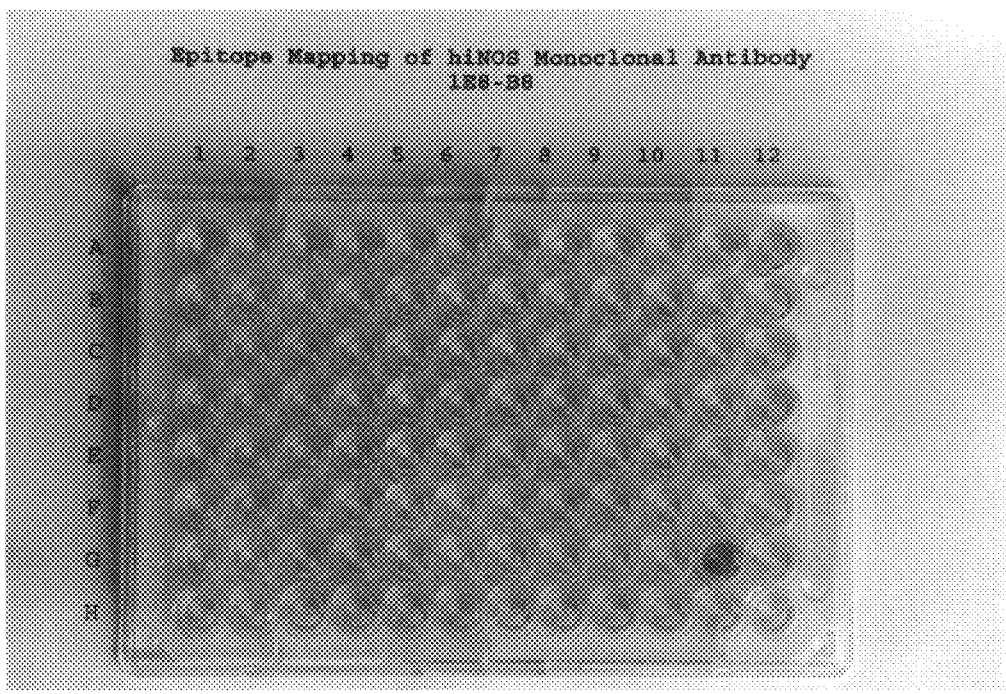
FIGS. 2–6 are photos of positively tested microtiter plates using the monoclonal antibodies of the present invention, as described in Example 3.
Figure 3:
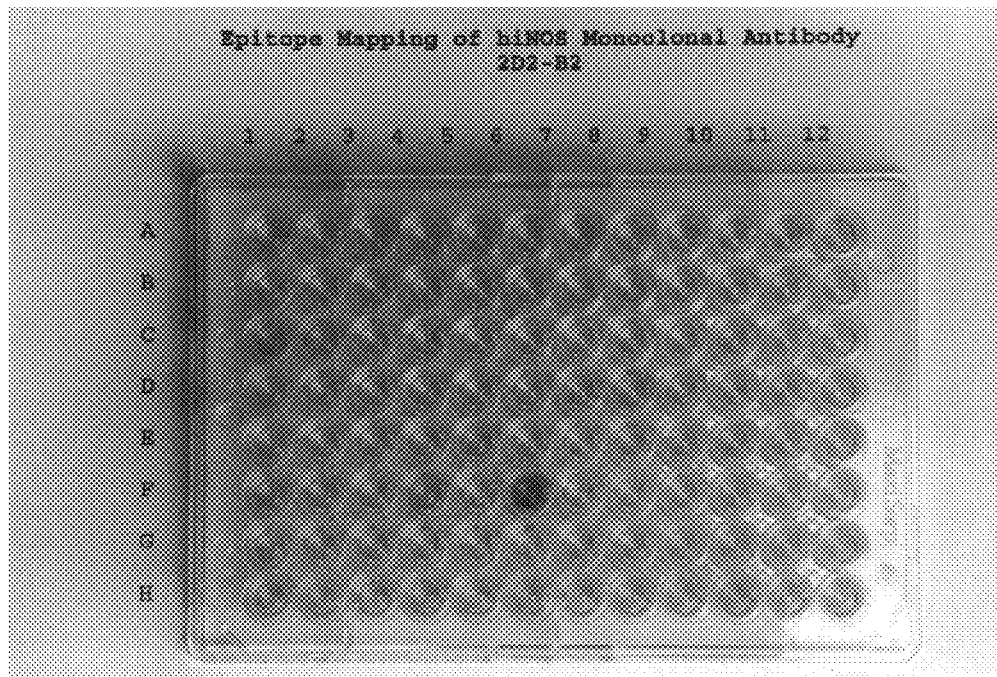
Figure 4:
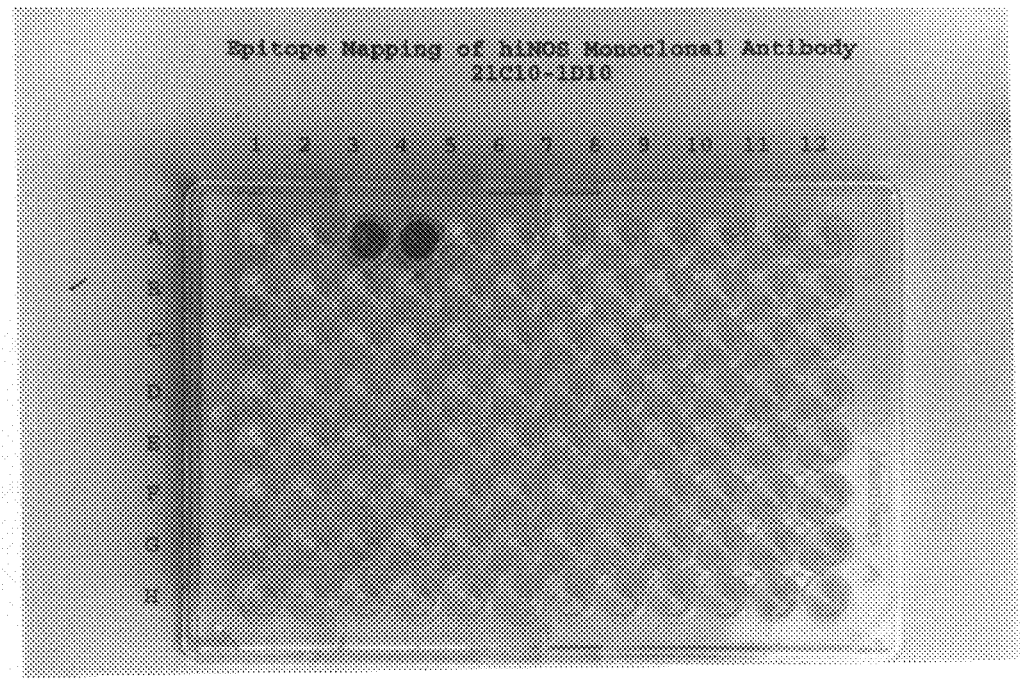
Figure 5:
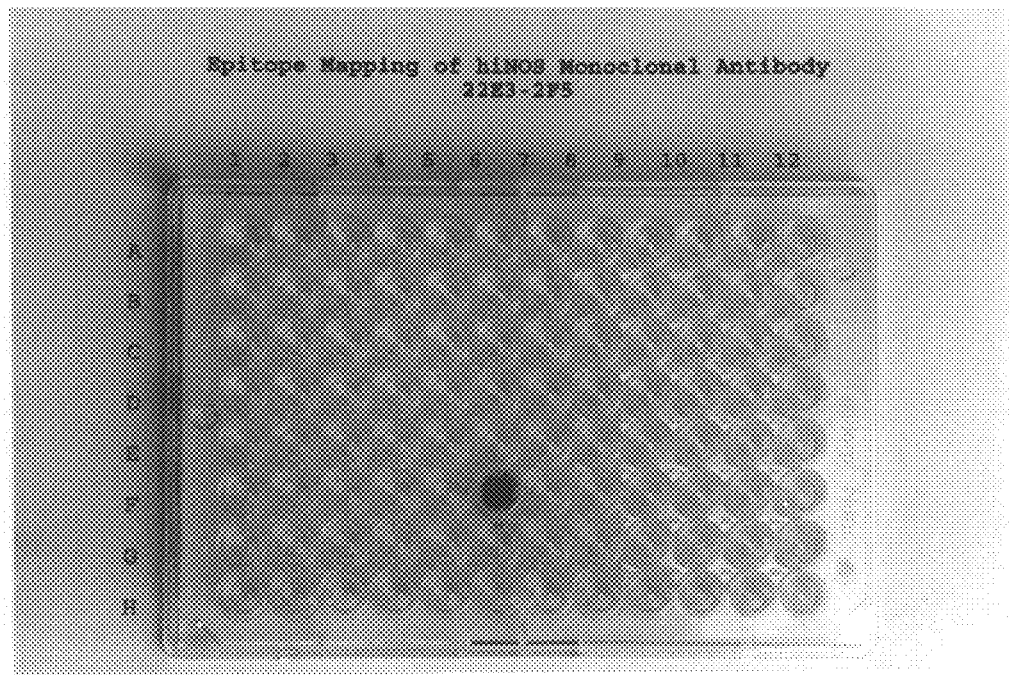
Figure 6:
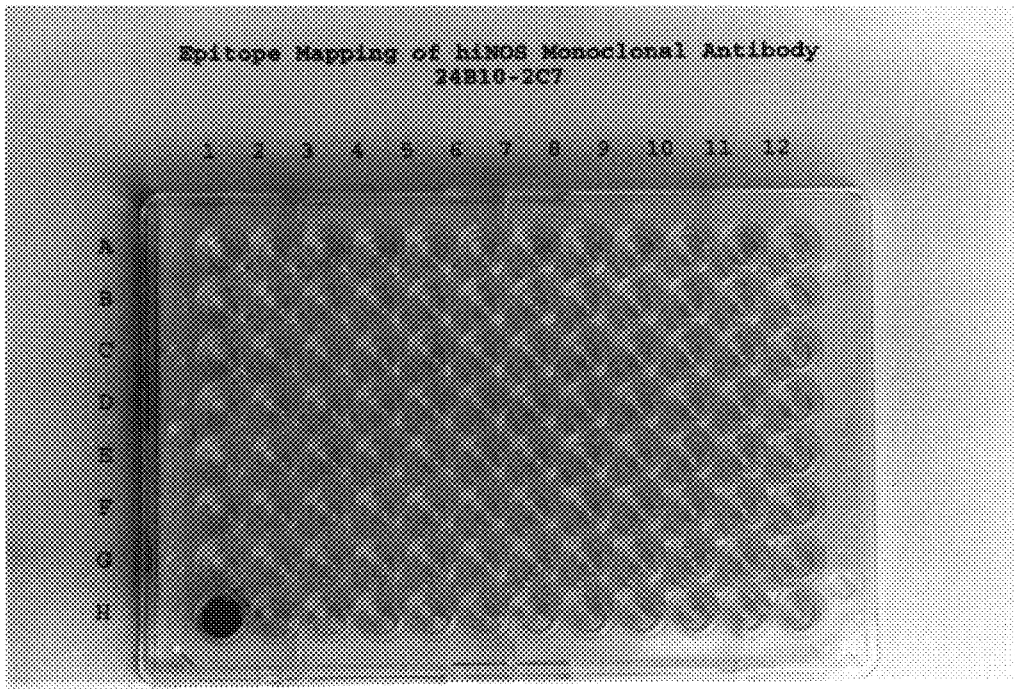

Various aspects of the present invention will evolve from the following detailed disclosure of the preferred embodiments thereof which should be referenced to the prior described drawings.

A panel of mouse monoclonal antibodies specific for the inducible form of human NOS (hiNOS) has been developed. The monoclonal antibodies were characterized by a number of different techniques including enzyme-linked immunosorbent assay (ELISA), western immunoblots, immunoprecipitation of $^{125}$I-hiNOS, and indirect immunofluorescent staining of cells. All the monoclonals were initially detected by ELISA, and all perform well in ELISA based assays. However, in all the other assay formats tested, some of the anti-hiNOS monoclonal antibodies worked well and others did not. Only one monoclonal antibody, 1E8-B8, has been found to perform well in all the assay formats tested. Others of the panel, such as 2A12-A4, 2H11-D11, 7D8-B3, and 21C10-1D10, perform well in most but not all of the assay formats examined. Thus, it will be necessary to test each of the monoclonal antibodies of the panel for suitability in any specific assay format or for any specific purpose. Such monoclonal antibodies have been used in immunoassays to determine the presence and quantity of hiNOS.

In addition, a separate panel of polyclonal rabbit antipeptide antibodies were developed. These monoclonal antibodies were elicited using whole hiNOS as immunogen. However, many, if not all, of these monoclonal antibodies could be developed using fragments or peptide analogues of hiNOS to elicit the initial immune response in mice. Such polyclonal antibodies were specific to the three isoforms of NOS (nNOS, iNOS, eNOS). The polyclonal antibodies were raised in rabbits to peptides of defined amino acid sequences, which mimicked either the amino terminal or the carboxyl terminal of each of the isoforms of human NOS. The peptides used in the polyclonal antibody production were synthesized according to known techniques.

In addition, purified human iNOS was employed to immunize mice and to develop a panel of monoclonal antibodies. The monoclonal antibodies could have been developed using protein fragments, fusion peptides and proteins, or peptide analogues of hiNOS to immunize mice and elicit an immune response to regions of hiNOS. Standard techniques were used to produce the hybridomas, clone the cells, and produce the monoclonal antibodies. The hybridomas and clones were screened by ELISA and western immunoblot and used in the production of monoclonal antibodies as culture supernatant. The monoclonal antibodies were characterized by standard techniques and were also isotyped. The monoclonal antibodies were then tested for their ability to inhibit the enzymatic activity of hiNOS. In order to determine which region of the protein each monoclonal antibody was recognizing, 96 overlapping peptides, each 18 amino acids long, were synthesized to cover the entire 1153 amino acid length structure of the hiNOS. Each peptide had a six amino acid long overlap with its nearest neighbors, except the carboxyl terminal peptide which had an 11 amino acid overlap with the prior peptide. The peptides were used to sensitize a specific well on microtiter plates, and culture supernatant or ascites from each clone was applied individually to the wells. The presence of bound monoclonal antibody was then determined. Specific regions of the iNOS protein were identified as being bound by the monoclonal antibodies. FIG. 1 represents peptide sequences which represent the specific regions of human iNOS which were determined to bind to some of the monoclonal antibodies of the present invention.

Once the region to which a specific monoclonal antibody was determined to bind, a computer search of the known protein databases was performed to find similar sequences of other proteins. This service is provided by the National Center for Biotechnology Information at the National Institutes of Health. A program named Basic Logistic Alignments Statistical Tool (BLAST) was employed in this search. The use of such tool is described in an article entitled "Basic Local Alignment Search Tool" by Altschul et al., Journal of Molecular Biology, Vol. 215 (1990). The following table represents the results of the computer search:

TABLE I

Sequence Homologies of Peptides to Regions of Proteins

| Peptide | Region | Sequence | | | | | P Value |
|---|---|---|---|---|---|---|---|
| A3 | human iNOS (25–42) | Asn | Asn | Asn | Val | Glu 5 | <2 × 10$^{-6}$ |
| | | Lys | Ala | Pro | Cys | Ala 10 | |
| | | Thr | Ser | Ser | Pro | Val 15 | |
| | | Thr | Gln | Asp | | | |
| | | SEQ ID NO: 1 | | | | | |
| | mouse iNOS (25–42) | Asn | Asn | Asn | Val | Lys 5 | <0.02 |
| | | Lys | Thr | Pro | Cys | Ala 15 | |
| | | Val | Leu | Ser | Pro | Thr 20 | |
| | | Ile | Gln | Asp | | | |
| | | SEQ ID NO: 2 | | | | | |
| | rat iNOS (25–42) | Asn | Asn | Asn | Val | Glu 5 | <0.03 |
| | | Lys | Thr | Pro | Gly | Ala 10 | |
| | | Ile | Pro | Ser | Pro | Thr 15 | |
| | | Thr | Gln | Asp | | | |
| | | SEQ ID NO: 3 | | | | | |
| A4 | human iNOS (37–54) | Ser | Pro | Val | Thr | Gln 5 | <2 × 10$^{-6}$ |
| | | Asp | Asp | Leu | Gln | Tyr 10 | |
| | | His | Asn | Leu | Ser | Lys 15 | |
| | | Gln | Gln | Asn | | | |
| | | SEQ ID NO: 4 | | | | | |
| F6 | human iNOS (781–798) | Pro | Ala | Leu | Val | Gln 5 | <1 × 10$^{-6}$ |
| | | Gly | Ile | Leu | Glu | Arg 10 | |
| | | Val | Val | Asp | Gly | Pro 15 | |
| | | Thr | Pro | His | | | |
| | | SEQ ID NO: 5 | | | | | |
| | mouse iNOS (776–792) | Xxx | Ala | Leu | Val | Gln 5 | <0.001 |
| | | Gly | Ile | Leu | Glu | Arg 10 | |
| | | Val | Val | Asp | Cys | Pro 15 | |
| | | Thr | Pro | His | | | |
| | | SEQ ID NO: 6 | | | | | |
| | rat iNOS (780-794) | Xxx | Xxx | Leu | Val | Gln 5 | <0.1 |
| | | Gly | Ile | Leu | Glu | Arg 10 | |
| | | Val | Val | Asp | Cys | Ser 15 | |
| | | Ser | Pro | Xxx | | | |
| | | SEQ ID NO: 7 | | | | | |
| G11 | human iNOS (985–1002) | Gly | Ile | Val | Pro | Phe 5 | <2 ×10$^{-8}$ |
| | | Arg | Ser | Phe | Trp | Gln 10 | |
| | | Gln | Arg | Leu | His | Asp | |

TABLE I-continued

Sequence Homologies of Peptides to Regions of Proteins

| Peptide | Region | Sequence | P Value |
|---|---|---|---|
| | | Ser Gln His 15 | |
| | | SEQ ID NO: 8 | |
| | mouse iNOS (978–995) | Gly Ile Ala Pro Phe 5 | $<1 \times 10^{-7}$ |
| | | Arg Ser Phe Trp Gln 10 | |
| | | Gln Arg Leu His Asp 15 | |
| | | Ser Gln His | |
| | | SEQ ID NO: 9 | |
| | rat iNOS (982–998) | Gly Ile Ala Pro Phe 5 | $<1 \times 10^{-7}$ |
| | | Arg Ser Phe Trp Gln 10 | |
| | | Gln Arg Leu His Asp 15 | |
| | | Ser Gln His | |
| | | SEQ ID NO: 10 | |
| | human nNOS (1256–1273) | Gly Ile Ala Pro Phe 5 | $<1 \times 10^{-4}$ |
| | | Arg Ser Phe Trp Gln 10 | |
| | | Gln Arg Gln Phe Asp 15 | |
| | | Ile Gln His | |
| | | SEQ ID NO: 11 | |
| | human eNOS (1017–1031) | Gly Ile Ala Pro Phe 5 | $<0.001$ |
| | | Arg Gly Phe Trp Gln 10 | |
| | | Glu Arg Leu His Asp 15 | |
| | | Xxx Xxx Xxx | |
| | | SEQ ID NO: 12 | |
| | bovine eNOS (1019–1033) | Gly Ile Ala Pro Phe 5 | $<0.001$ |
| | | Arg Gly Phe Trp Gln 10 | |
| | | Glu Arg Leu His Asp 15 | |
| | | Xxx Xxx Xxx | |
| | | SEQ ID NO: 13 | |
| H1 | human iNOS (1009–1026) | Arg Met Thr Leu Val 5 | $<1 \times 10^{-6}$ |
| | | Phe Gly Cys Arg Arg 10 | |
| | | Pro Asp Glu Asp His 15 | |
| | | Ile Tyr Gln | |
| | | SEQ ID NO: 14 | |
| | rat iNOS (1006–1023) | Arg Met Thr Leu Val 5 | $<1 \times 10^{-4}$ |
| | | Phe Gly Cys Arg His 10 | |
| | | Pro Glu Glu Asp His 15 | |
| | | Leu Tyr Gln | |
| | | SEQ ID NO: 15 | |
| | mouse iNOS (1002–1019) | Arg Met Ser Leu Val 5 | $<2 \times 10^{-4}$ |
| | | Phe Gly Cys Arg His 10 | |
| | | Pro Glu Glu Asp His 15 | |
| | | Leu Tyr Gln | |
| | | SEQ ID NO: 16 | |

Where "Xxx" represents mismatched amino acids which were not used in the BLAST calculations.

"P Value" represents the probability of dissimilarity. In other words, the smaller the value, the more likely the probability of there being a match. For example, the results of the BLAST calculations for peptide A3 in Table I found complete sequence homology with hiNOS (25–42). This was expected since this is the region of hiNOS that this peptide was built to mimic. The computer search only found sequence homology with two other proteins. One sequence homology concern mouse iNOS (25–42) with a P Value of less than 0.02. The other sequence homology was rat iNOS (25–42) with a P Value of less than 0.03. No sequence homology was found to any other proteins in the databases with a P Value of less than 0.1. The search of the protein database for sequence homology with peptide A4 found homology only with human iNOS (37–54) which is the region mimicked by the peptide. No region of any other protein in the databases was determined to match this sequence with a P Value of less than 0.1 (i.e., the probability that there is a difference is greater than 99.9%). The search for sequence homology to peptide F6 which is hiNOS (781–798) found sequence homology with human iNOS and with mouse and rat iNOS. No homology was found during this search to any other protein with a P Value of less than 0.1. However, the search for sequence homology with peptide G11, which is hiNOS (985–1002), found homology to a number of proteins in Table I. These included mouse and rat iNOS, human nNOS (1256–1273), human eNOS (1017–1031), and bovine eNOS (1019–1033). The computer search for sequence homology to peptide H1, which is hiNOS (1009–1026), found homology only with rat and mouse iNOS. No other sequence homology was found with a P Value less than 0.5. It should be noted that a small amount of homology was found with human eNOS and human nNOS, but the P Values are greater than 0.5.

The sequences from each of the 18-mers to which monoclonal antibodies are found to bind, i.e., peptides A3 (PS-5103), A4 (PS-5104), F6 (PS-5166), G11 (PS-5183), and H1 (PS-5185), Table I, were used to design and make a series of epitope mapping peptides for these regions. A series of four truncation peptides from the amino acid terminal end of the 18-mers, as well as a series of four truncations from the carboxyl terminal of each of the 18-mers were fashioned. Various degrees of truncation were used to determine the minimum lengths of amino acids to which some of binding to the monoclonal antibodies of the present invention could bind. FIG. 7 represents amino acid sequences showing such truncated peptides which were bound by some of the monoclonal antibodies of the present invention.

In addition, a number of peptide homologue were designed and synthesized based on the BLAST search. These peptide homologue were used to characterize the specificity of the monoclonal antibodies to proteins other than hiNOS. For example, such other proteins included hNOS, heNOS, mouse iNOS, and rat iNOS.

An immunoassay was set-up to determine the presence and quantity of hiNOS in samples. Purified goat anti-rabbit IgG was used to sensitize microtiter plates. The plates were blocked with bovine seral bumine (BSA). Rabbit polyclonal anti-peptide antibody was added and allowed to bind as the "catch" antibody in order to bind hiNOS in samples. Various mouse monoclonal antibodies from the panel of Table III were tested for their ability to detect and quantitate hiNOS. Clones 1E8-B8, 21C10-1D10, 2A12-A4, and others of Table III were found to work in this format. It is believed that other formats such as the formation of strips for rapid detection of iNOS may be applicable to the assay of the present invention.

In addition to use in sandwich ELISAs, the panel of monoclonal antibodies of Table III were tested for their ability to detect hiNOS in samples by western immunoblot techniques. In this technique, cells in culture were induced with a cytokine/LPS mix. The latter technique induced the production of iNOS by the cells which was detectable in western immunoblots by the monoclonal antibodies of the present invention.

In addition to use in sandwich ELISAs and western immunoblots, each of the monoclonal antibodies in the panel of Table III was tested for its ability of immunoprecipitate hiNOS. This was tested by radioimiunoassay (RIA) techniques using $^{125}$I-labeled hiNOS. Ten of the 20 different monoclonal antibodies in the panel were determined to immunoprecipitate hiNOS by this method. Of the ten positives found, monoclonal antibodies 2H11-D11, 5B3-E6, and 21C10-1D10 were found to be the best at immunoprecipitating the radiolabeled protein.

The ability of the monoclonal antibodies in Table III to recognize and bind to iNOS in fixed cells was also investigated. Induction of iNOS production was examined in three very different types of cultured cells by indirect immunofluorescent staining of the induced cells using the anti-hiNOS monoclonal antibodies as the primary antibody. The three types of induced cultured cells tested were A-172 (a human glioblastoma cell line), RAW 264.7 (a mouse macrophage cell line), and normal human monocytes isolated from blood. Three monoclonal antibodies, 1E8-B8, 2A12-A4, and 2H11-D11, were found to perform particularly well in this assay format: other monoclonals from the panel performed less well or did not stain the cells.

While in the foregoing, embodiments of the present invention have been set forth in considerable detail for the purposes of making a complete disclosure of the invention, it may be apparent to those of skill in the art that numerous changes may be made in such detail without departing from the spirit and principles of the invention.

The following examples are presented as being illustrative of the invention, but are not intended to be limiting of the invention or any embodiment thereof, unless specified hereinafter.

EXAMPLE 1

PRODUCTION OF POLYCLONAL ANTIBODIES

Peptides of defined amino acid sequences were prepared, which mimicked either the amino terminal or the carboxyl terminal of each of the isoforms of human NOS. Each peptide was synthesized by solid phase peptide synthesis utilizing the from protecting strategy. The synthetic peptides were cleaved from the solid support resin, isolated, and purified by standard procedures including preparative HPLC. They were analyzed for purity by analytical HPLC.

1. Each synthetic peptide was conjugated onto a carrier protein, keyhole limpet hemocyanin (KHL), using either the EDAC or sulfo-MBS chemistries to construct the immunogens for the elicitation of antibodies.

2. Each peptide/protein conjugate was used as an immunogen in rabbits. The different immunogens were employed to immunize groups of 2–4 rabbits each. The rabbits were immunized, boosted, and bled following a standard protocol developed for the production of anti-peptide antibodies in rabbits.

3. The antiserum obtained from each bleed of each rabbit was tested by ELISA for the production of antibodies specific for the synthetic peptide analogue. Those antisera found positive for production of antibodies specific for the peptide portion of the immunogen were then assessed for their ability to recognize the whole protein.

TABLE II

Synthetic Peptides Used as Immunogens

| Batch # & segment | Sequence Location | Amino Acid Sequence |
|---|---|---|
| PS-1656 hnNOS[2–16, Cys$^{17}$] | human nNOS: amino terminal | Glu Asp His Met Phe 5<br>Gly Val Gln Gln Ile 10<br>Gln Pro Asn Val Ile 15<br>Cys<br>SEQ ID NO: 17 |
| PS-1653 hnNoS [Cys$^{1410}$-1411-1433] | human nNOS: carboxyl terminal | Cys Arg Leu Arg Ser 5<br>Glu Ser Ile Ala Phe 10<br>Ile Glu Glu Ser Lys 15<br>Lys Asp Thr Asp Glu 20<br>Val Phe Ser Ser<br>SEQ ID NO: 18 |
| PS-1673B hiNOS [2–21, Ser$^2$ ] | human iNOS: amino terminal | Ala Ser Pro Trp Lys 5<br>Phe Leu Phe Lys Thr 10<br>Lys Phe His Gln Tyr 15<br>Ala Met Asn Gly Glu 20<br>SEQ ID NO: 19 |
| PS-16143 hiNOS [Cys$^{1136}$-1137-1153] | human iNOS: carboxyl terminal | Cys Lys Lys Asp Arg 5<br>Val Ala Val Gln Pro 10<br>Ser Ser Leu Glu Met 15<br>Ser Ala Leu<br>SEQ ID NO: 20 |
| PS-1686 heNOS[Cap-2–12, Cys$^{13}$] | human eNOS: amino terminal with caproic acid attached | Cap-Gly Asn Leu Lys<br>Ser Val Ala Gln Glu 5<br>Pro Gly Cys 10<br>SEQ ID NO: 21 |
| PS-1687 heNOS[2–12, Cys$^{13}$] | human eNOS: amino terminal without caproic acid attached | Gly Asn Leu Lys Ser 5<br>Val Ala Gln Glu Pro 10<br>Gly Cys<br>SEQ ID NO: 22 |
| PS-1648 heNOS [Cys$^{1181}$-1182-1203] | human eNOS: carboxyl terminal | Cys Glu Arg Gln Leu 5<br>Arg Glu Ala Val Pro 10<br>Trp Ala Phe Asp Pro 15<br>Pro Gly Ser Asp Thr 20<br>Asn Ser Pro<br>SEQ ID NO: 23 |

EXAMPLE 2

PRODUCTION OF MONOCLONAL ANTIBODIES

Purified human INOS was used to immunize mice and develop a panel of monoclonal antibodies. Standard techniques were used to produce the hybridomas, clone the cells, and produce the monoclonal antibodies. Such techniques are described in a protocol entitled "Production of Monoclonal Antibodies", Current Protocols in Immunology (1991). Briefly, spleens from immunized mice were aseptically removed, splenocytes were isolated and were fused with SP2/0—Ag 14 myeloma cells with polyethylene glycol. Hybridomas were screened by ELISA for production of mouse IgG or IgM antibodies to hiNOS. Positive hybrids were expanded and cloned via limiting dilution. The clones were screened by ELISA and western immunoblot techniques. Positive clones were expanded, frozen down in liquid nitrogen for cryopreservation, and used for the production of monoclonal antibodies as culture supernatant, as well as ascites fluid from Balb/C female mice.

The monoclonal antibodies produced by the various clones were characterized by a number of different techniques. These include ELISA, western immunoblot, immunoprecipitation of $^{125}$I-hiNOS (I.P.), and indirect immunofluorescent staining of cells (I.F.A.). The monoclonal antibodies were also isotyped. Table III represents these results:

TABLE III

Characteristics af hiNOS Monoclonal Antibodies

| Clone | Isotype | ELISA | Western Immuno-Blot | I.P. | I.F.A. |
|---|---|---|---|---|---|
| 1A11-F7 | Mouse IgG1 kappa | + | − | + | ND |
| 1E8-B8 | Mouse IgG1 kappa | + | + | + | + |
| 2A1-F8 | Mouse IgG2a kappa | + | + | + | ND |
| 2A12-A4 | Mouse IgG1 kappa | + | + | − | + |
| 2D2-B2 | Mouse IgG1 kappa | + | − | − | weak |
| 2D10-F12 | Mouse IgG2A kappa | + | − | − | − |
| 2H11-D11 | Mouse IgM Kappa | + | − | + | + |
| 4E8-G9 | Mouse IgG2B Kappa | + | − | − | ND |
| 5B3-E6 | Mouse IgG1 kappa | + | − | + | weak |
| 5D5-H10 | Mouse IgG1 kappa | + | + | − | ND |
| 6A12-A12 | Mouse IgG2a Kappa | + | − | + | ND |
| 6G12-H7 | Mouse IgG1 kappa | + | + | − | ND |
| 7D8-B3 | Mouse IgM | + | − | + | + |
| 21C10-1D10 | Mouse IgG2B Kappa | + | + | + | − |
| 21D4-2A8 | Mouse IgM | + | − | + | + |
| 21H11-2D2 | Mouse IgG | + | − | + | ND |
| 22E3-2F5 | Mouse IgG1 Kappa | + | + | − | − |
| 23G6-2A12 | Mouse IgG1 Kappa | + | + | − | − |
| 24B10-2C7 | Mouse IgG1 Kappa | + | − | − | − |
| 24H9-1F3 | Mouse IgG1 Kappa | + | + | − | − |

Where "ND" indicates "not determined"; "+" is "positive"; "−" is "negative"; and "weak" represents binding at only very high monoclonal antibody concentrations.

EXAMPLE 3

EPITOPE MAPPING OF MONOCLONAL ANTIBODIES

In order to determine which region of the protein each monoclonal antibody of Example 2 was recognizing, 96 overlapping peptides were synthesized to cover the entire 1153 amino acid length structure of hiNOS. All peptides were 18 amino acids long (18-mers) and were synthesized as carboxyl terminal amides. Serine was substituted for all the naturally occurring cysteine residues in the structure, and each peptide had a six amino acid long overlap with its nearest neighbors, except the carboxyl terminal peptide which had an 11 amino acid overlap with the prior peptide. The peptides were used to epitope map the panel of monoclonal antibodies by ELISA techniques. Each peptide was used to sensitize a specific well on a series of microtiter plates. The culture supernatant or ascites from each monoclonal antibody was then applied individually to all the wells of a sensitized plate. The wells were then tested for the presence of bound mouse monoclonal antibody. Representative results that were obtained for this series of experiments are shown in FIGS. 2–6 and are summarized in Table IV, below:

TABLE IV

Epitope Mapping of Monoclonal Antibodies to hiNOS

| Monoclonal Antibody | Binds to | Sequence | Region |
|---|---|---|---|
| 1E8-B8 | G11 = PS-5183 | Gly Ile Val Pro Phe 5<br>Arg Ser Phe Trp Gln 10<br>Gln Arg Leu His Asp 15<br>Ser Gln His<br>SEQ ID NO: 24 | 985–1002 |
| 2A12-A4 | G11 = PS-5183 | Gly Ile Val Pro Phe 5<br>Arg Ser Phe Trp Gln 10<br>Gln Arg Leu His Asp 15<br>Ser Gln His<br>SEQ ID NO: 25 | 985–1002 |
| 6G12-H7 | A4 = PS-5104 | Ser Pro Val Thr Gln 5<br>Asp Asp Leu Gln Tyr 10<br>His Asn Leu Ser Lys 15<br>Gln Gln Asn<br>SEQ ID NO: 26 | 37–54 |
| 2D2-B2 | F6 = | Pro Ala Leu Val Gln | 781–798 |

TABLE IV-continued

Epitope Mapping of Monoclonal Antibodies to hiNOS

| Monoclonal Antibody | Binds to | Sequence | Region |
|---|---|---|---|
| | PS-5166 | Gly Ile Leu Glu Arg 5<br>Val Val Asp Gly Pro 10<br>Thr Pro His 15<br>SEQ ID NO: 27 | |
| 21C10-1D10 | A3 =<br>PS-5103 & | Asn Asn Asn Val Glu 5<br>Lys Ala Pro Ser Ala 10<br>Thr Ser Ser Pro Val 15<br>Thr Gln Asp<br>SEQ ID NO: 28 | 25–42 |
| | A4 =<br>PS-5104 | Ser Pro Val Thr Gln 5<br>Asp Asp Leu Gln Tyr 10<br>His Asn Leu Ser Lys 15<br>Gln Gln Asn<br>SEQ ID NO: 29 | 37–54 |
| 22E3-2F5 | F6 =<br>PS-5166 | Pro Ala Leu Val Gln 5<br>Gly Ile Leu Glu Arg 10<br>Val Val Asp Gly Pro 15<br>Thr Pro His<br>SEQ ID NO: 30 | 781–798 |
| 24B10-2C7 | H1 =<br>PS-5185 | Arg Met Thr Leu Val 5<br>Phe Gly Ser Arg Arg 10<br>Pro Asp Glu Asp His<br>Ile Tyr Gln 15<br>SEQ ID NO: 31 | 1009–1026 |

EXAMPLE 4

EPITOPE MAPPING AND SPECIFICITY CHARACTERAATION WITH SYNTHETHIC PEPTIDES

The sequence from each of the 18-mers to which monoclonal antibodies were found to bind (peptides A3, A4, F6, G11 and H1, Table IV) were used to design and make a series of epitope mapping peptides for these regions. Also, homologs to iNOS found by the BLAST search were employed to characterize the specificity of the iNOS monoclonal antibodies. A series of four truncation peptides from the amino terminal end of each of the 18-mers as well as a series of four truncations from the carboxyl terminal of each of the 18-mers were made. Each series deleted three amino acids in turn from either the carboxyl or amino terminal of the 18-mers. This resulted in two series of truncation peptides for each 18-mers which were successively shorter by three amino acids from each end. Table V and FIGS. 7A-7D and FIG. 8 list the truncation peptides and peptide homologs to hINOS that were built, the latter were from regions of human nNOS, mouse and rat iNOS, and human eNOS, if any sequence homology was found to these regions by the BLAST computer search, hereinbefore discussed:

TABLE V

Truncated and Homalog Epitope Mapping Peptides

| Peptide | AA Segment | Sequence | Monoclonal Binding |
|---|---|---|---|
| PS-5103 | (A3) locus<br>human iNOS(25–42) | Asn Asn Asn Val Glu 5<br>Lys Ala Pro Ser Ala 10<br>Thr Ser Ser Pro Val 15<br>Thr Gln Asp-amide<br>SEQ ID NO: 32 | 21C10-1D10<br>+ |
| PS-5241 | mouse iNOS(25–42) | Asn Asn Asn Val Lys 5<br>Lys Thr Pro Ser Ala 10<br>Val Leu Ser Pro Thr 15<br>Ile Gln Asp-amide<br>SEQ ID NO: 33 | weak |
| PS-5242 | rat iNOS(25–42) | Asn Asn Asn Val Glu 5<br>Lys Thr Pro Gly Ala 10<br>Ile Pro Ser Pro Thr 15<br>Thr Gln Asp-amide<br>SEQ ID NO: 34 | – |
| PS-5243 | human iNOS(28–42) | Val Glu Lys Ala Pro 5<br>Ser Ala Thr Ser Ser | – |

TABLE V-continued

Truncated and Homolog Epitope Mapping Peptides

| Peptide | AA Segment | Sequence | Monoclonal Binding | |
|---|---|---|---|---|
| | | Pro Val Thr Gln 10<br>Asp-amide<br>15<br>SEQ ID NO: 35 | | |
| PS-5244 | human iNOS(31–42) | Ala Pro Ser Ala Thr 5<br>Ser Ser Pro Val Thr 10<br>Gln Asp-amide<br>SEQ ID NO: 36 | – | |
| PS-5245 | human iNOS(34–42) | Ala Thr Ser Ser Pro 5<br>Val Thr Gln Asp-amide<br>SEQ ID NO: 37 | – | |
| PS-5246 | human iNOS(37–42) | Ser Pro Val Thr Gln 5<br>Asp-amide<br>SEQ ID NO: 38 | – | |
| PS-5247 | human iNOS(25–39) | Asn Asn Asn Val Glu 5<br>Lys Ala Pro Ser Ala 10<br>Thr Ser Ser Pro Val- 15<br>amide<br>SEQ ID NO: 39 | – | |
| PS-5248 | human iNOS(25–36) | Asn Asn Asn Val Glu 5<br>Lys Ala Pro Ser Ala 10<br>Thr Ser-amide<br>SEQ ID NO: 40 | – | |
| PS-5249 | human iNOS(25–33) | Asn Asn Asn Val Glu 5<br>Lys Ala Pro Ser-amide<br>SEQ ID NO: 41 | – | |
| PS-5250 | human iNOS(25–30) | Asn Asn Asn Val Glu 5<br>Lys-amide<br>SEQ ID NO: 42 | – | |
| PS-5104 | (A4) locus<br>human iNOS(37–54) | Ser Pro Val Thr Gln 5<br>Asp Asp Leu Gln Tyr 10<br>His Asn Leu Ser Lys 15<br>Gln Gln Asn-amide<br>SEQ ID NO: 43 | 6G12-H7<br>+ | 21C 10-1D10<br>+ |
| PS-5261 | human iNOS(40–54) | Thr Gln Asp Asp Leu 5<br>Gln Tyr His Asn Leu 10<br>Ser Lys Gln Gln Asn- 15<br>amide<br>SEQ ID NO: 44 | + | – |
| PS-5262 | human iNOS(43–54) | Asp Leu Gln Tyr His 5<br>Asn Leu Ser Lys Gln 10<br>Gln Asn-amide<br>SEQ ID NO: 45 | weak | – |
| PS-5263 | human iNOS(46–54) | Tyr His Asn Leu Ser 5<br>Lys Gln Gln Asn-amide<br>SEQ ID NO: 46 | – | – |
| PS-5264 | human iNOS(49–54) | Leu Ser Lys Gln Gln 5<br>Asn-amide<br>SEQ ID NO: 47 | – | – |

TABLE V-continued

Truncated and Homolog Epitope Mapping Peptides

| Peptide | AA Segment | Sequence | Monoclonal Binding | |
|---|---|---|---|---|
| PS-5265 | human iNOS(37–51) | Ser Pro Val Thr Gln 5<br>Asp Asp Leu Gln Tyr 10<br>His Asn Leu Ser Lys- 15<br>amide<br>SEQ ID NO: 48 | + | + |
| PS-5266 | human iNOS(37–48) | Ser Pro Val Thr Gln 5<br>Asp Asp Leu Gln Tyr 10<br>His Asn-amide<br>SEQ ID NO: 49 | – | – |
| PS-5267 | human iNOS(37–45) | Ser Pro Val Thr Gln 5<br>Asp Asp Leu Gln-amide<br>SEQ ID NO: 50 | – | – |
| PS-5268 | human iNOS(37–42) | Ser Pro Val Thr Gln 5<br>Asp-amide<br>SEQ ID NO: 51 | – | – |
| PS-5166 | (F6) locus<br>human iNOS(781–798) | Pro Ala Leu Val Gln 5<br>Gly Ile Leu Glu Arg 10<br>Val Val Asp Gly Pro 15<br>Thr Pro His-amide<br>SEQ ID NO: 52 | 2D2-B2<br>+ | |
| PS-5221 | human eNOS(806–824) | Pro Gly Leu Val Glu 5<br>Ala Leu Leu Ser Arg 10<br>Val Glu Asp Pro Pro 15<br>Ala Pro Thr Glu-amide<br>SEQ ID NO: 53 | – | |
| PS-5222 | human iNOS(784–798) | Val Gln Gly Ile Leu 5<br>Glu Arg Val Val Asp 10<br>Gly Pro Thr Pro His- 15<br>amide<br>SEQ ID NO: 54 | + | |
| PS-5223 | human iNOS(787–798) | Ile Leu Glu Arg Val 5<br>Val Asp Gly Pro Thr 10<br>Pro His-amide<br>SEQ ID NO: 55 | – | |
| PS-5224 | human iNOS(790–798) | Arg Val Val Asp Gly 5<br>Pro Thr Pro His-amide<br>SEQ ID NO: 56 | – | |
| PS-5225 | human iNOS(793–798) | Asp Gly Pro Thr Pro 5<br>His-amide<br>SEQ ID NO: 57 | – | |

TABLE V-continued

Truncated and Homolog Epitope Mapping Peptides

| Peptide | AA Segment | Sequence | Monoclonal Binding | |
|---|---|---|---|---|
| PS-5226 | human iNOS(781–794) | Pro Ala Leu Val Gln 5 Gly Ile Leu Glu Arg 10 Val Val Asp Gly-amide SEQ ID NO: 58 | + | |
| PS-5227 | human iNOS(781–792) | Pro Ala Leu Val Gln 5 Gly Ile Leu Glu Arg 10 Val Val-amide SEQ ID NO: 59 | + | |
| PS-5228 | human iNOS(781–789) | Pro Ala Leu Val Gln 5 Gly Ile Leu Glu-amide SEQ ID NO: 60 | weak | |
| PS-5229 | human iNOS(781–786) | Pro Ala Leu Val Gln 5 Gly-amide SEQ ID NO: 61 | – | |
| PS-5183 | (G11) locus human iNOS(985–1002) | Gly Ile Val Pro Phe 5 Arg Ser Phe Trp Gln 10 Gln Arg Leu His Asp 15 Ser Gln His-amide SEQ ID NO: 62 | 1E8-B8 + | 2A12-A4 + |
| PS-5201 | human nNOS (1256–1273) | Gly Ile Ala Pro Phe 5 Arg Ser Phe Trp Gln 10 Gln Arg Gln Phe Asp 15 Ile Gln His-amide SEQ ID NO: 63 | + | + |
| PS-5202 | human eNOS (1017–1031) | Gly Ile Ala Pro Phe 5 Arg Gly Phe Trp Gln 10 Glu Arg Leu His Asp-15 amide SEQ ID NO: 64 | – | – |
| PS-5203 | human iNOS(988–1002) | Pro Phe Arg Ser Phe 5 Trp Gln Gln Arg Leu 10 His Asp Ser Gln His-15 amide SEQ ID NO: 65 | weak | + |
| PS-5204 | human iNOS(991–1002) | Ser Phe Trp Gln Gln 5 Arg Leu His Asp Ser 10 Gln His-amide SEQ ID NO: 66 | – | – |
| PS-5205 | human iNOS(994–1002) | Gln Gln Arg Leu His 5 Asp Ser Gln His-amide SEQ ID NO: 67 | – | – |
| PS-5206 | human iNOS(997–1002) | His Asp Ser Gln His-amide | – | – |

TABLE V-continued

Truncated and Homolog Epitope Mapping Peptides

| Peptide | AA Segment | Sequence | Monoclonal Binding |
|---|---|---|---|
| | | SEQ ID NO: 68 | |
| PS-5207 | human iNOS(985–998) | Gly Ile Val Pro Phe 5 Arg Ser Phe Trp Gln 10 Gln Arg Leu His Asp-amide 15 | – – |
| | | SEQ ID NO: 69 | |
| PS-5208 | human iNOS(985–996) | Gly Ile Val Pro Phe 5 Arg Ser Phe Trp Gln 10 Gln Arg-amide | – – |
| | | SEQ ID NO: 70 | |
| PS-5209 | human iNOS(985–993) | Gly Ile Val Pro Phe 5 Arg Ser Phe Trp-amide | – – |
| | | SEQ ID NO: 71 | |
| PS-5210 | human iNOS(985–990) | Gly Ile Val Pro Phe 5 Arg-amide | – – |
| | | SEQ ID NO: 72 | |
| PS-5185 | (H1) locus human iNOS(1009–1026) | Arg Met Thr Leu Val 5 Phe Gly Ser Arg Arg 10 Pro Asp Glu Asp His 15 Ile Tyr Gln-amide | 24B10-2C7 + |
| | | SEQ ID NO: 73 | |
| PS-5281 | human eNOS(1041–1057) | Met Thr Leu Val Phe 5 Gly Ser Arg Ser Ser 10 Gln Leu Asp His Leu 15 Tyr Arg-amide | – |
| | | SEQ ID NO: 74 | |
| PS-5282 | human nNOS(1281–1297) | Met Val Leu Val Phe 5 Gly Ser Arg Gln Ser 10 Lys Ile Asp His Ile 15 Tyr Arg-amide | – |
| | | SEQ ID NO: 75 | |
| PS-5283 | human iNOS(1012–1026) | Leu Val Phe Gly Ser 5 Arg Arg Pro Asp Glu 10 Asp His Ile Tyr Gln-amide 15 | + |
| | | SEQ ID NO: 76 | |
| PS-5284 | human iNOS(1015–1026) | Gly Ser Arg Arg Pro 5 Asp Glu Asp His Ile 10 Tyr Gln-amide | + |
| | | SEQ ID NO: 77 | |
| PS-5285 | human iNOS(1018–1026) | Arg Pro Asp Glu Asp 5 His Ile Tyr Gln-amide | weak |
| | | SEQ ID NO: 78 | |
| PS-5286 | human iNOS(1021–1026) | Glu Asp His Ile Tyr 5 Gln-amide | – |
| | | SEQ ID NO: 79 | |
| PS-5287 | human iNOS(1009–1023) | Arg Met Thr Leu Val 5 | – |

TABLE V-continued

Truncated and Homolog Epitope Mapping Peptides

| Peptide | AA Segment | Sequence | Monoclonal Binding |
|---|---|---|---|
| | | Phe Gly Ser Arg Arg 10 Pro Asp Glu Asp His- 15 amide SEQ ID NO: 80 | |
| PS-5288 | human iNOS(1009–1020) | Arg Met Thr Leu Val 5 Phe Gly Ser Arg Arg 10 Pro-amide SEQ ID NO: 81 | − |
| PS-5289 | human iNOS(1009–1017) | Arg Met Thr Leu Val 5 Phe Gly Ser Arg- amide SEQ ID NO: 82 | − |
| PS-5290 | human iNOS(1009–1014) | Arg Met Thr Leu Val 5 Phe-amide SEQ ID NO: 83 | − |

Where "+" represents positive binding, "−" represents no binding, and "weak" represents binding at only very high monoclonal antibody concentrations.

The ability of the monoclonal antibodies to bind to the various truncation analogues or to the nNOS and eNOS analogues were tested by ELISA in a similar format to that which was used to screen the original ninety-six 18-mers.

At the A-3 locus, monoclonal antibody 2C10-1D10 would only bind strongly to peptide A-3 (PS-5103) and weakly to the mouse homolog miNOS (25–42), (PS-5241). 21C10-1D10 would not bind to any of the truncated peptides nor to the rat homolog riNOS (25–42), (PS-5242).

At the A4 locus, two monoclonal antibodies were determined to bind during the initial screening (6G12-H7 and 21C10-1D10). These showed differing specificities to the truncated peptides. Monoclonal antibody 6G12-H7 was found to bind strongly to A4 (PS-5104), and two truncated analogues, PS-5261 and PS-5265: it also bound weakly to PS-5262. This shows that the original 18-mers should be able to be shortened to at least a 12-mers with the sequence Thr Gln Asp Asp Leu Gln Tyr His Asn Leu Ser Lys SEQ ID NO: 84 and still be able to bind to this peptide analogue of the whole protein. In contrast, monoclonal antibody 21C10-1D10 bound only to the original 18-mer A4 (PS-5104) and to the hiNOS (37–51) peptide sequence (PS-5265), which is truncated three residues on the carboxyl terminus.

At the F6 locus, monoclonal antibody 2D2-B2 was found to bind strongly peptide F6 (PS-5166) and three of its truncated analogues, PS-5222, PS-5226, and PS-5227. It bound PS5228 weakly and to the human eNOS (806–824), PS-5221, not at all. However, from the results obtained with the truncation peptides, the epitope should be contained in the sequence Val Gln Gly Ile Leu Glu Arg Val Val SEQ ID NO: 85.

At the G-11 locus, two monoclonal antibodies were found to bind during the initial screening, 1E8-B8 and 2A12-A4. When these two were tested for binding to the truncation series and two homologs, a similar pattern of recognition was found for both monoclonals. Both bound strongly to peptide G-11 (PS-5183), as expected, and both recognized the homolog human nNOS (1256–1273), PS-5201, though the binding was much less than for G-11. Each recognized PS-5203, the first of the amino terminal truncation series peptides, but the binding of 1E8-B8 was much weaker than that observed for 2A12-A4.

Finally, at the H1 locus, monoclonal antibody 24B10-2C7 was found to bind to H1 (PS-5185). This monoclonal did not recognize either the human eNOS or nNOS homologs, PS-5281 and PS-5282, respectively, but it did bind strongly to the first two amino terminal truncation series peptides, PS-5283 and PS-5284. Monoclonal 24B10-2C7 also bound weakly to the next shorter amino terminal truncation peptide, PS-5285. These results indicate that this monoclonal antibody recognized a sequence located in the carboxyl terminal region of peptide H-1 (PS-5185).

EXAMPLE 5

SANDWICH ELISA TO DETERMINE QUANTITY OF HINOS IN SAMPLES

Figure 9:
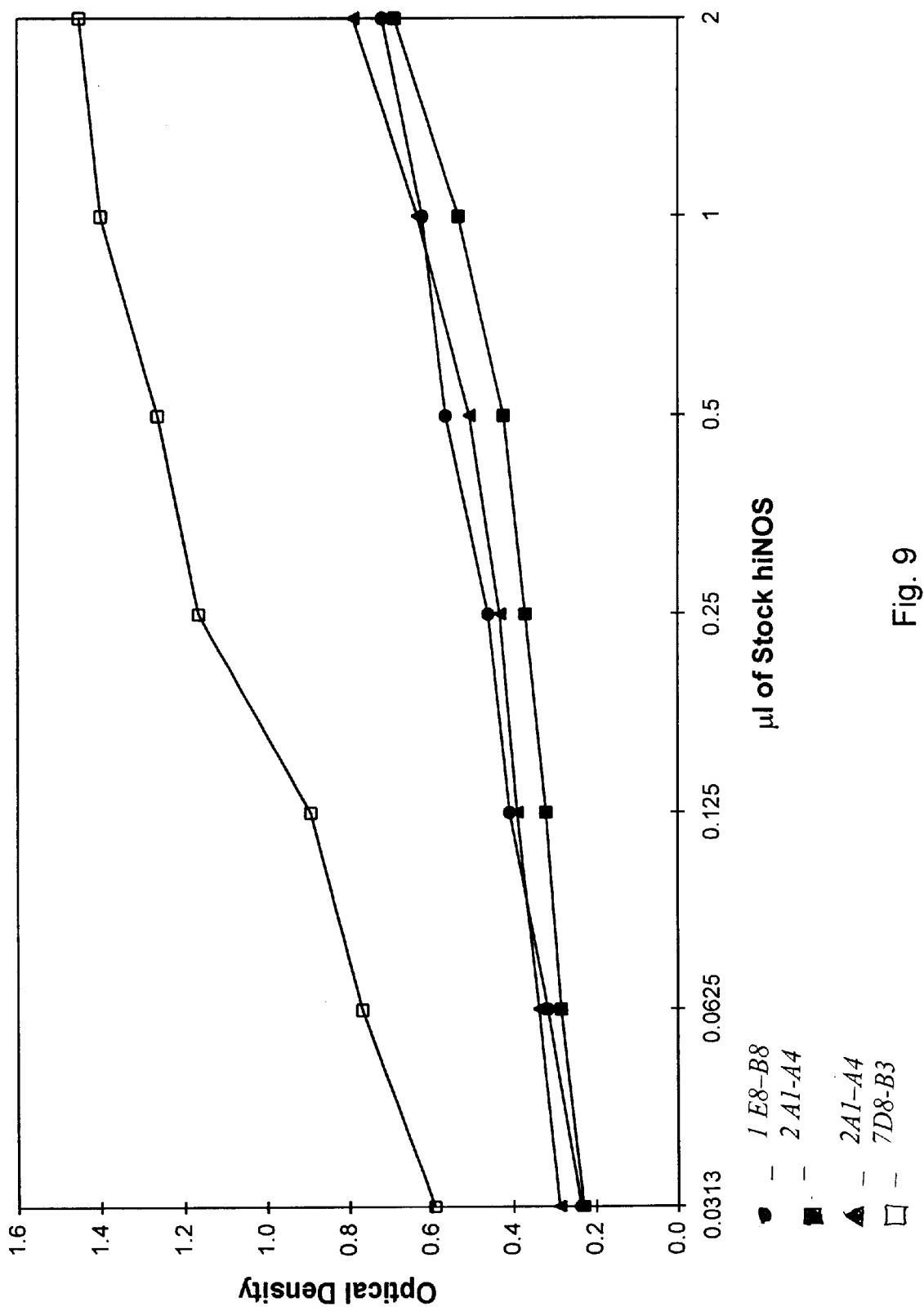
FIG. 9 is a graph representing a sandwich ELISA that measures hiNOS using polyclonal rabbit anti-peptide antibodies and four mouse monoclonal antibodies.

Polyclonal rabbit anti peptide iNOS antisera was used as a "catch" antibody in the initial attempt to develop a sandwich ELISA for hiNOS. In this format affinity purified goat anti-rabbit IgG at 1 $\mu$gm per well in 100 $\mu$l was used to sensitize microtiter plates. Following this the plates were blocked with bovine serum albumin (BSA). Rabbit polyclonal anti-peptide antibody (specific for the carboxyl terminal of hiNOS) was added and allowed to bind. This was used as "catch" antibody to bind hiNOS in samples. Various mouse monoclonal from the panel of Table III were tested for their ability to detect and/or quantitate hiNOS in samples, illustrated in FIG. 9. The results shows that clones 1E8-B8, 21C10-1D10, 2A1-A4, and 7D8-B3 were found to work in this assay format. However, in order to eliminate the necessity of repeatedly producing polyclonal rabbit anti-peptide antibody, which needs extensive characterization, a sandwich ELISA was designed using monoclonal antibodies from the panel developed to hiNOS, Table III, as both the "catch" and detection antibodies. In this assay format affinity purified goat anti-mouse IgG2A, IgG2B, or IgM was used to sensitize the microtiter plates. The "catch" monoclonal antibody was then added; either 2A1-F8, 6A12-A12, 2

Figure 10:
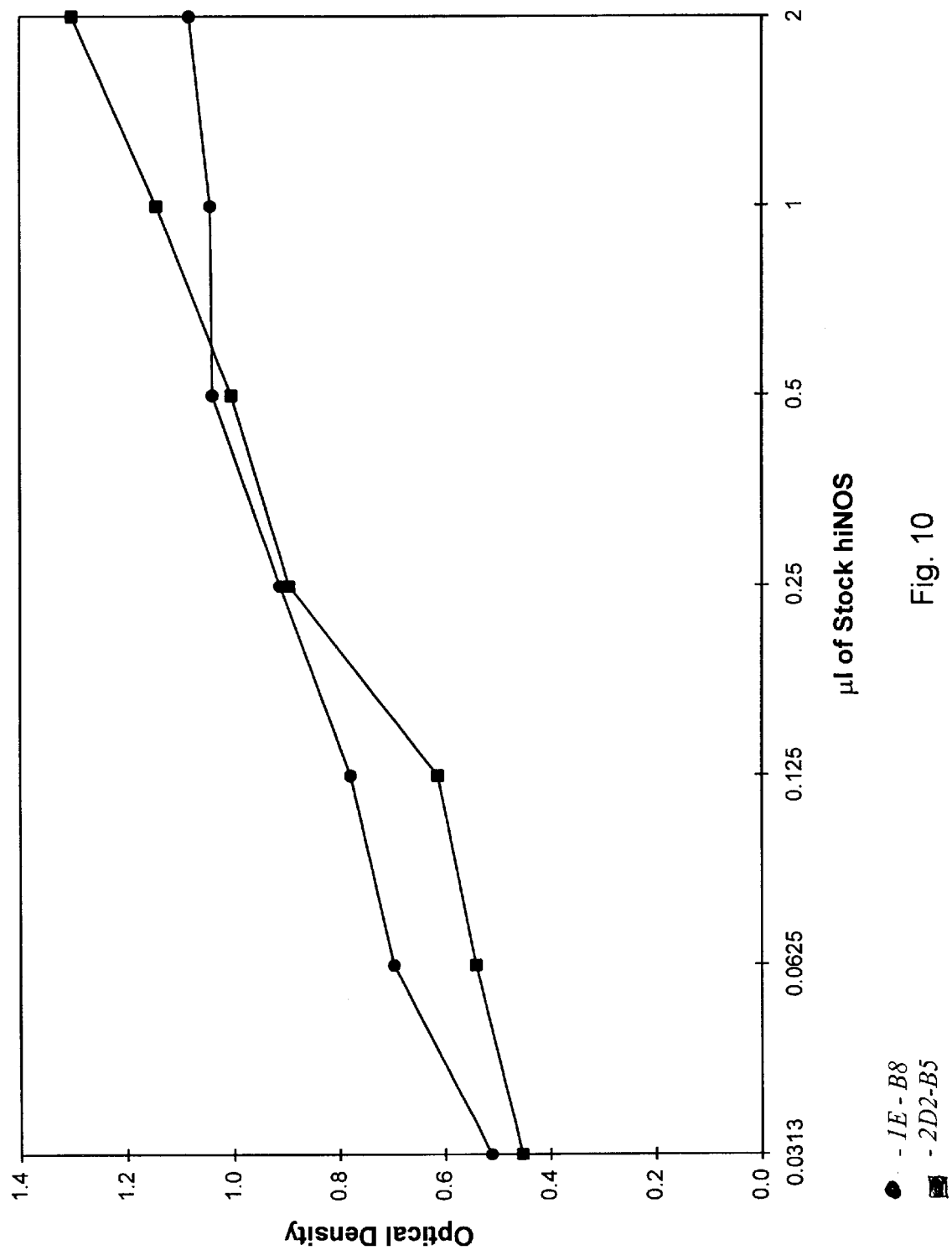
FIG. 10 is a graph representing a sandwich ELISA that measures hiNOS using mouse IgG2b monoclonal antibody 21C10-1D10 and two mouse IgG1 monoclonal antibodies.
Figure 11:
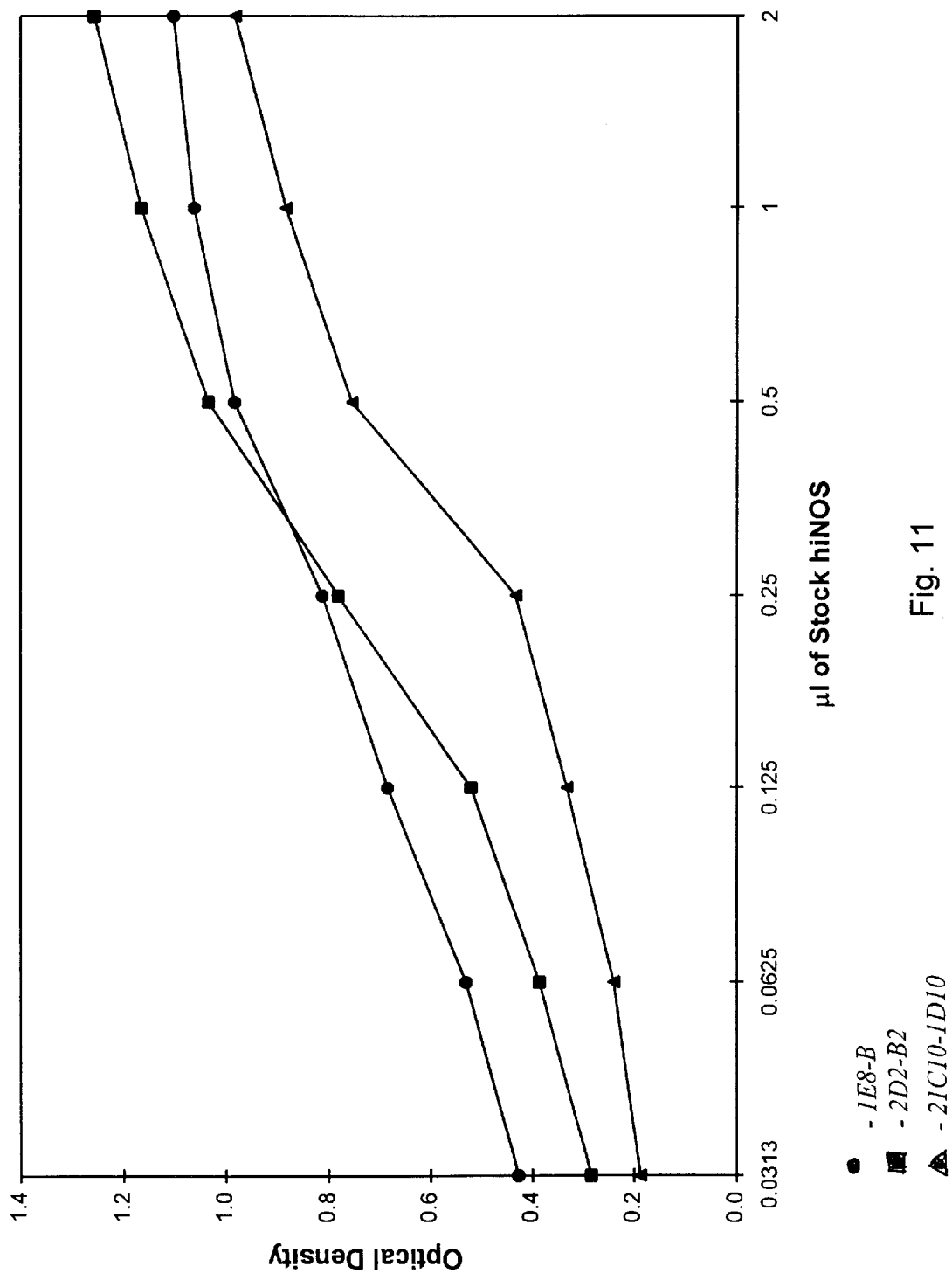
FIG. 11 is a graph representing a sandwich ELISA that measures hiNOS using mouse IgM monoclonal antibody 7D8-B3 and three mouse IgG monoclonal antibodies.

1C10-1D10, or one of IgM class monoclonals. The plate was then blocked with BSA. Samples known to contain hiNOS were then applied to the microtiter plates. Following this, they were then thoroughly washed. The detection monoclonal antibody used was one from a different immunoglobulin class. In the case of monoclonal antibody 21C10-1D10, which is an IgG2b, mouse IgG1 monoclonal antibodies were used as detection antibodies, for example 1E8-B8 and 2D2-B5, shown in FIG. 10. In the case of the "catch" monoclonal antibody being an IgM class antibody, any of the mouse IgG clones could be used as detection antibody; this includes 1E8-B8 (IgG1), 2D2-B2 (IgG1), and 21C10-1D10 (IgG2B), per FIG. 11. As is evident, a monoclonal based antibody sandwich ELISA can be produced using the panel of monoclonal antibodies of Table III. The necessity for using a polyclonal "catch" antibody can be eliminated by employing different immunoglobulin class monoclonal antibodies from the panel of mouse monoclonal antibodies developed to hiNOS.

EXAMPLE 6

WESTERN IMMUNOBLOTS

Figure 12:
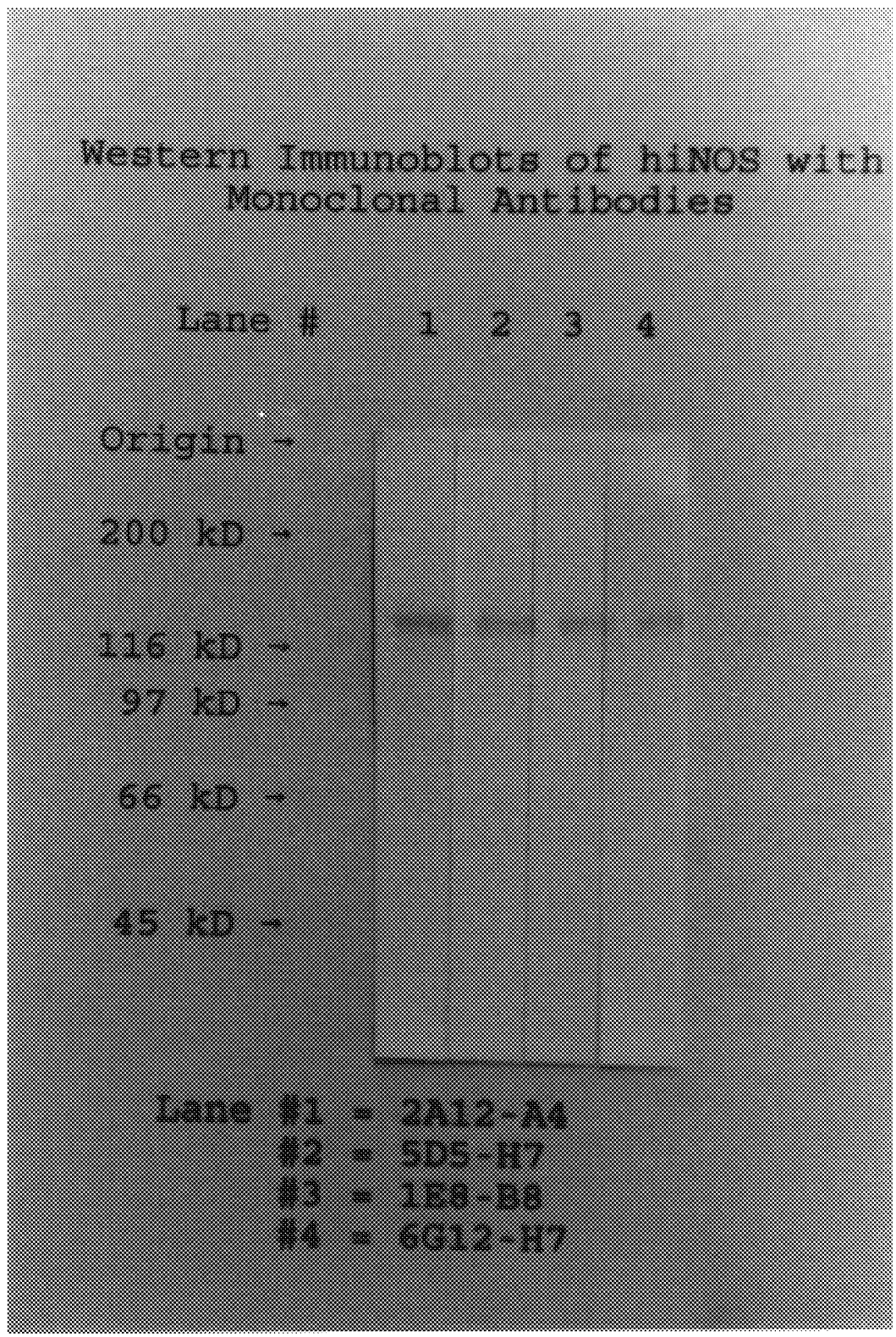
FIG. 12 is a photograph of a western immunoblot of hiNOS using four different primary monoclonal antibodies and HRP-conjugated goat anti-mouse IgG secondary antibody.

In addition to use in sandwich ELISAs, the panel of monoclonal antibodies of Table III was tested for their ability to detect hiNOS in samples by western immunoblot techniques. Samples were electrophoresed on 7.5% SDS-PAGE gels which separates the proteins by molecular weight. The proteins were transferred onto PVDF membranes, and the membranes were blocked with evaporated goats milk diluted 1:4 with PBS/Tween 20 buffer. The primary anti-hiNOS monoclonal antibodies were bound, and then the membranes were developed using HRP-conjugated goat anti-mouse IgG antibody, shown in FIG. 12. The monoclonal antibodies have also been tested in western blots using cell lysates obtained from cells which have been reported to contain INOS following induction with cytokine/LPS mix. Cell lines A-172 and RAW 264.7 were purchased from American Type Culture Collection of Rockville, Md. (ATCC), were expanded, and cells were harvested before and after induction with a cytokine/LPS mix, FIGS. 13 and 14. Such cytotoxic mix is described in the Geller et al., article, hereinbefore noted, as a cytokine/LPS mixture. The cell pellets were thoroughly washed after harvesting with PBS to remove extraneous proteins. The cells were lysed by two freeze-thaw cycles and sonification. The cell lysates were diluted 1:2 with SDS-PAGE sample buffer and boiled for ten minutes. The samples were electrophoresed on 7.5% gels as described above. The uninduced cells did not contain INOS whereas, after induction with the cytokine/LPS mix, a band at 130kd was present. This shows that the cytokine/LPS mix had induced iNOS and that the monoclonal antibodies of Table III can detect iNOS in unknown samples in the western blot format.

Figure 13:
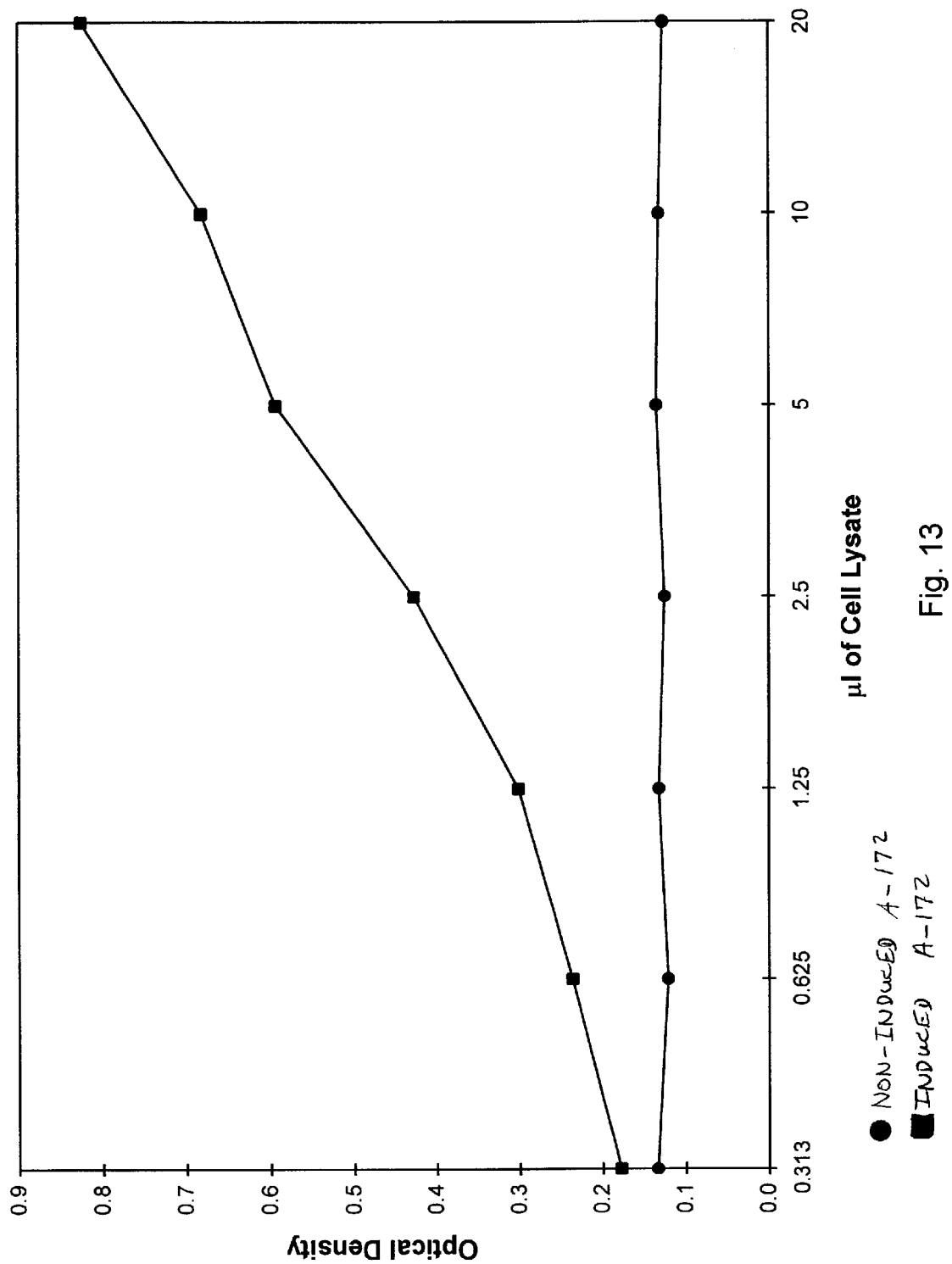
FIG. 13 is a graph representing a sandwich ELISA that measures hiNOS in non-induced and induced A-172 cell lysates using a mouse IgM monoclonal catch antibody, 7D8-B3, and a mouse IgG1 monoclonal detection antibody, 1E8-B8.
Figure 14:
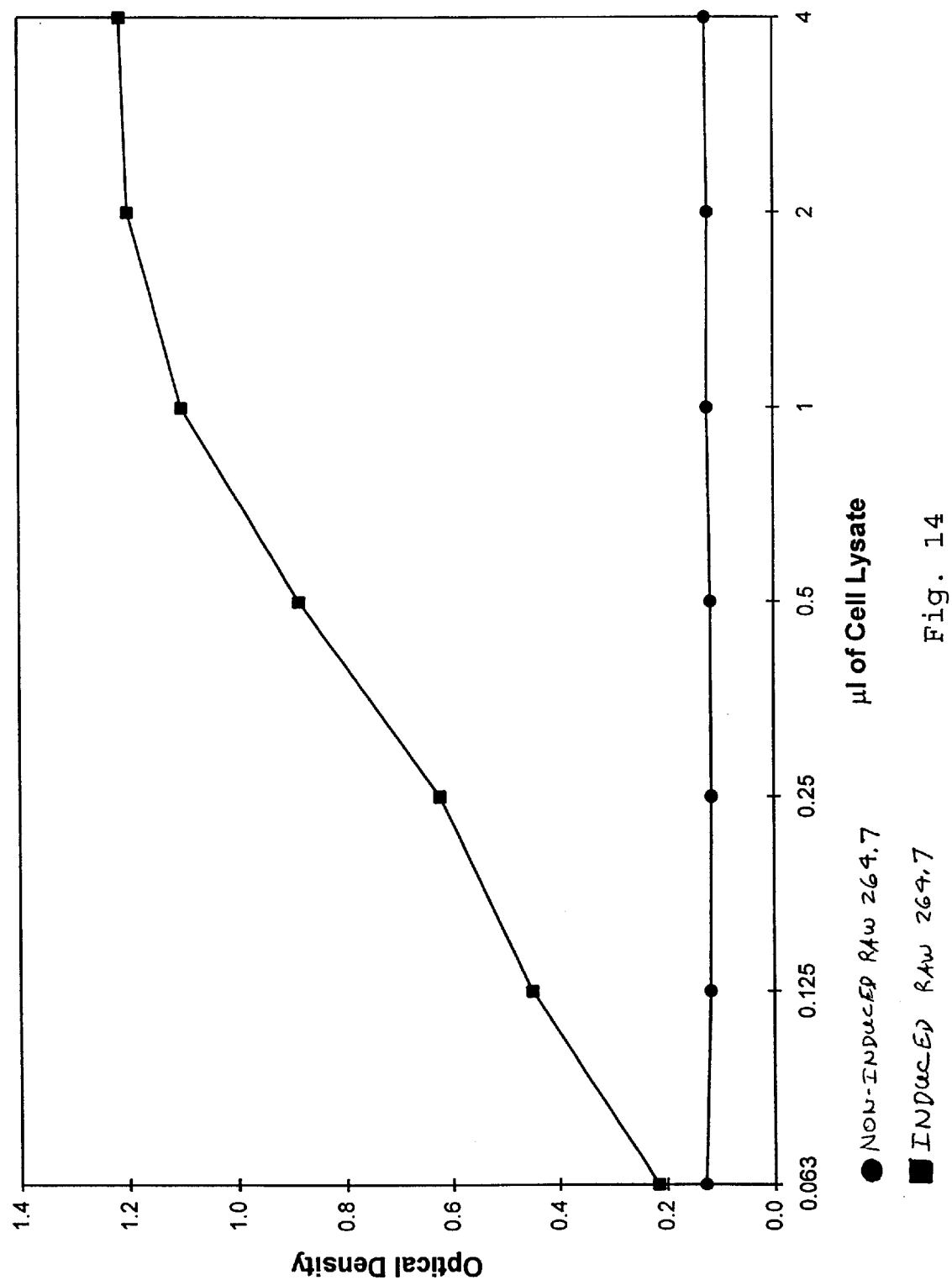
FIG. 14 is a graph representing a sandwich ELISA that measures iNOS in non-induced and induced RAW 264.7 cell lysates using mouse IgM monoclonal catch antibody, 7D8-B3, and mouse IgG1 monoclonal detection antibody, 1E8-B8.

In addition to examining these induced cell lysates by western immunoblots, they were tested by the sandwich ELISA procedure of Example 5 to determine if iNOS could be detected and/or quantitated. The results of such ELISA tests as illustrated in FIGS. 13 and 14 clearly indicated no iNOS was present in the uninduced cells, whereas after induction with the cytokine/LPS mix a substantial amount of iNOS was present.

EXAMPLE 7

IMMUNOFLUORESCENT STAINING OF INDUCED CELLS

Figure 15:
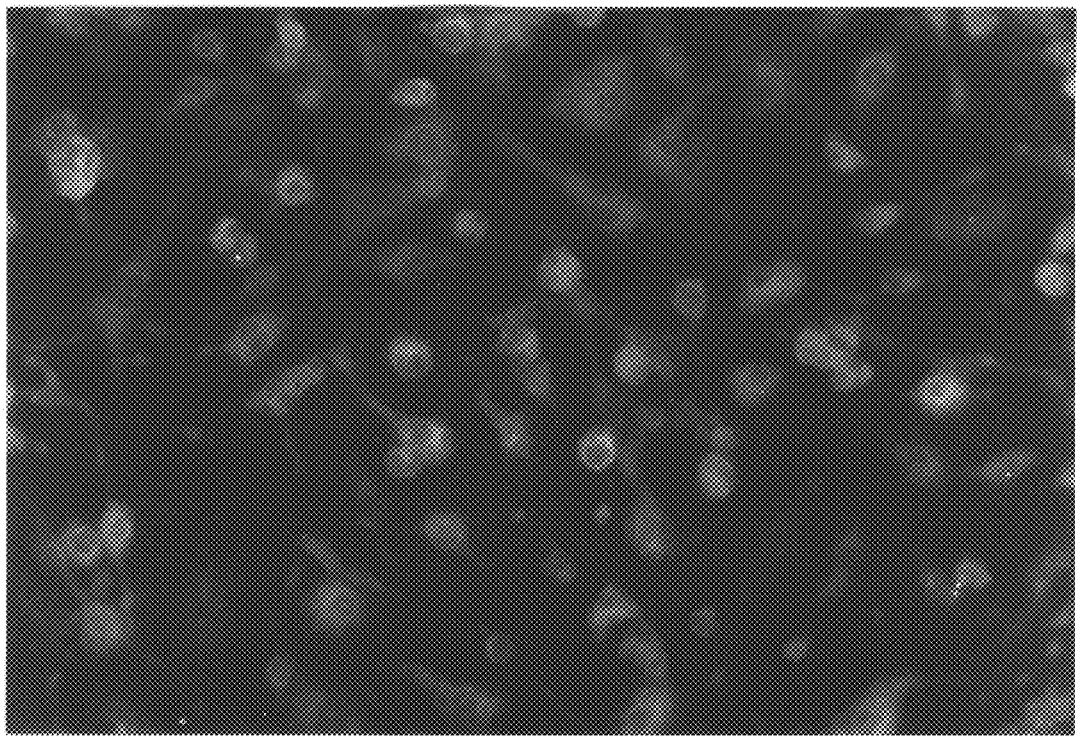
FIG. 15 is a photograph showing the indirect immunofluorescent staining of induced A-172 cells with mouse IgG1 monoclonal antibody 1E8-B8 magnified 1600×.
Figure 16:
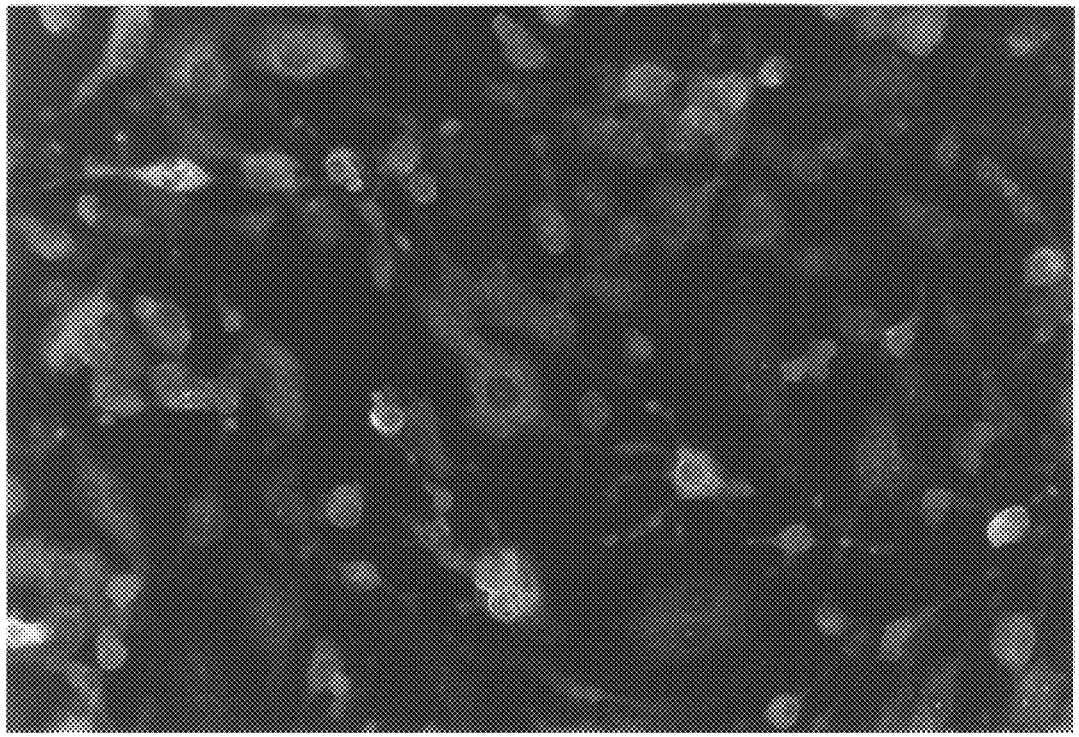
FIG. 16 is a photograph showing the indirect immunofluorescent staining of induced A-172 cells with mouse IgG1 monoclonal antibody 2A12-A4 magnified 1600×.
Figure 17:
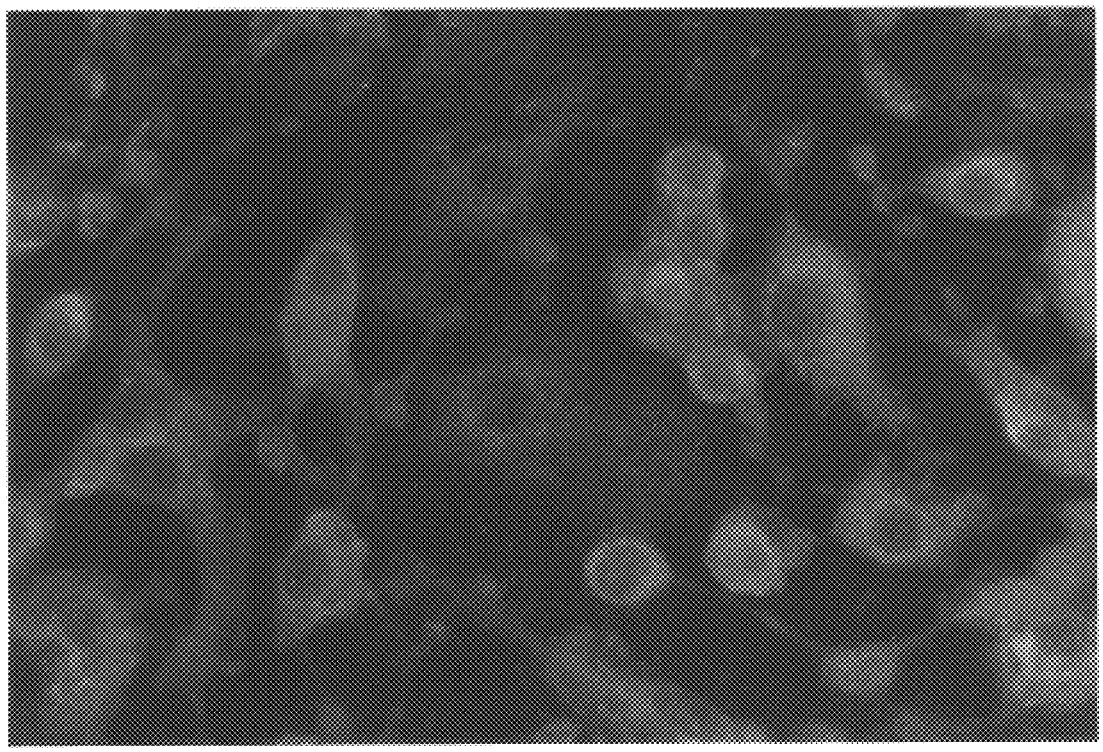
FIG. 17 is a photograph showing the indirect immunofluorescent staining of induced A-172 cells with mouse IgM monoclonal antibody 2H11-D11 magnified 1600×.
Figure 18:
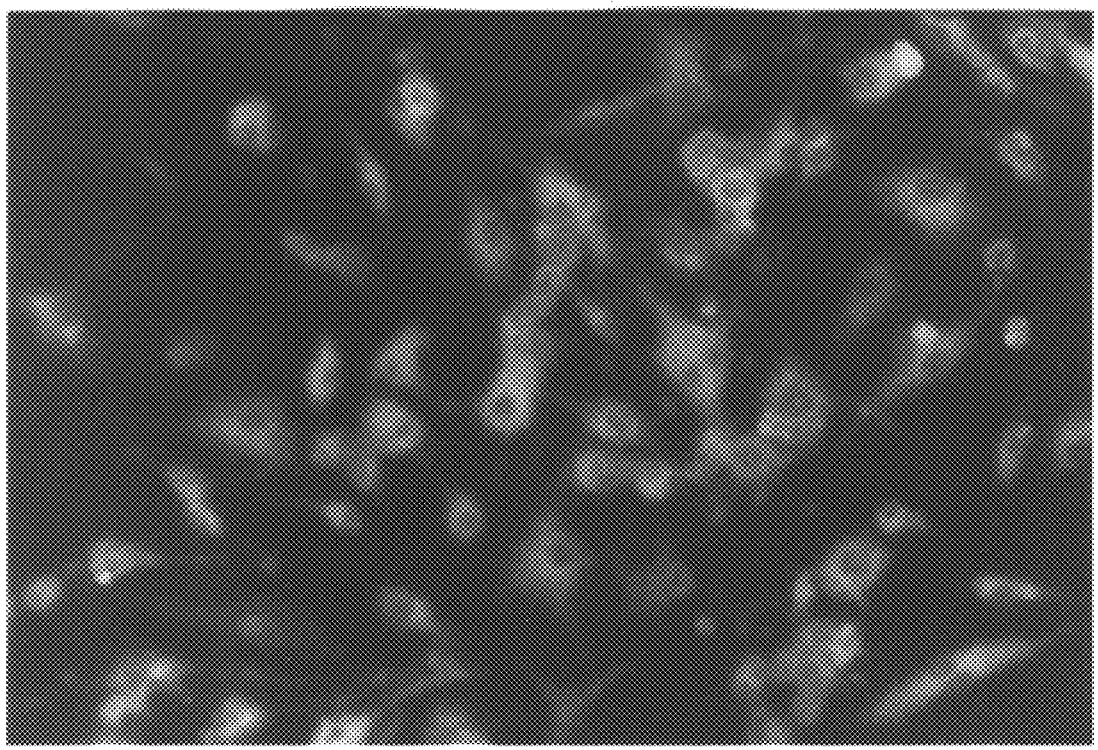
FIG. 18 is a photograph showing the indirect immunofluorescent staining of induced RAW 264.7 cells with mouse IgG1 monoclonal antibody 1E8-B8 magnified 1600×.
Figure 19:
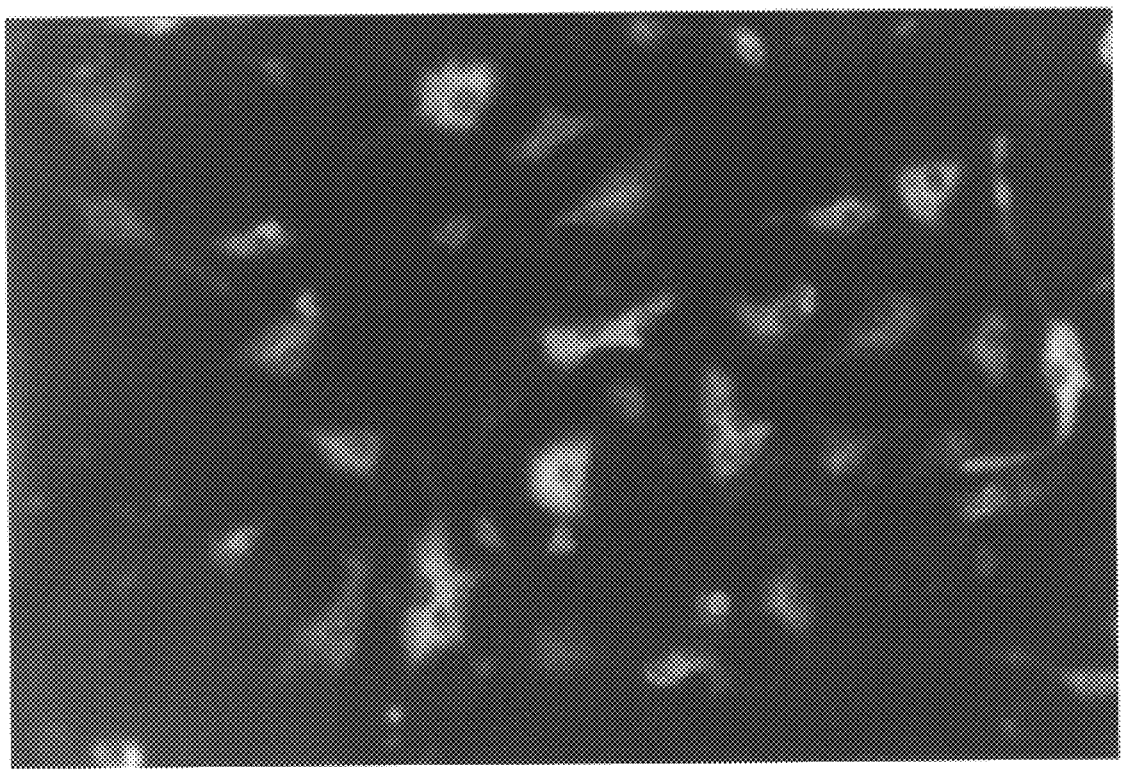
FIG. 19 is a photograph showing the indirect immunofluorescent staining of induced RAW 264.7 cells with mouse IgG1 monoclonal antibody 2A12-A4 magnified 1600×.
Figure 20:
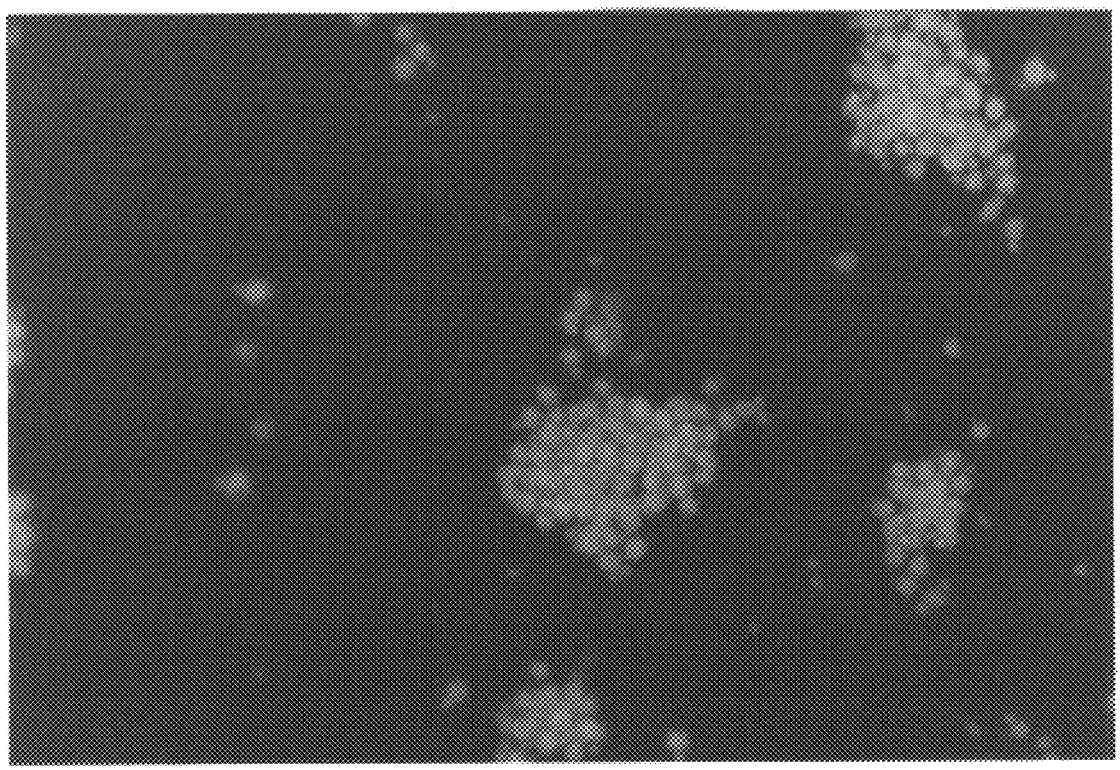
FIG. 20 is a photograph showing the indirect immunofluorescent staining of induced human monocytes with mouse IgG1 monoclonal antibody 1E8-B8 magnified 1600×.
Figure 21:
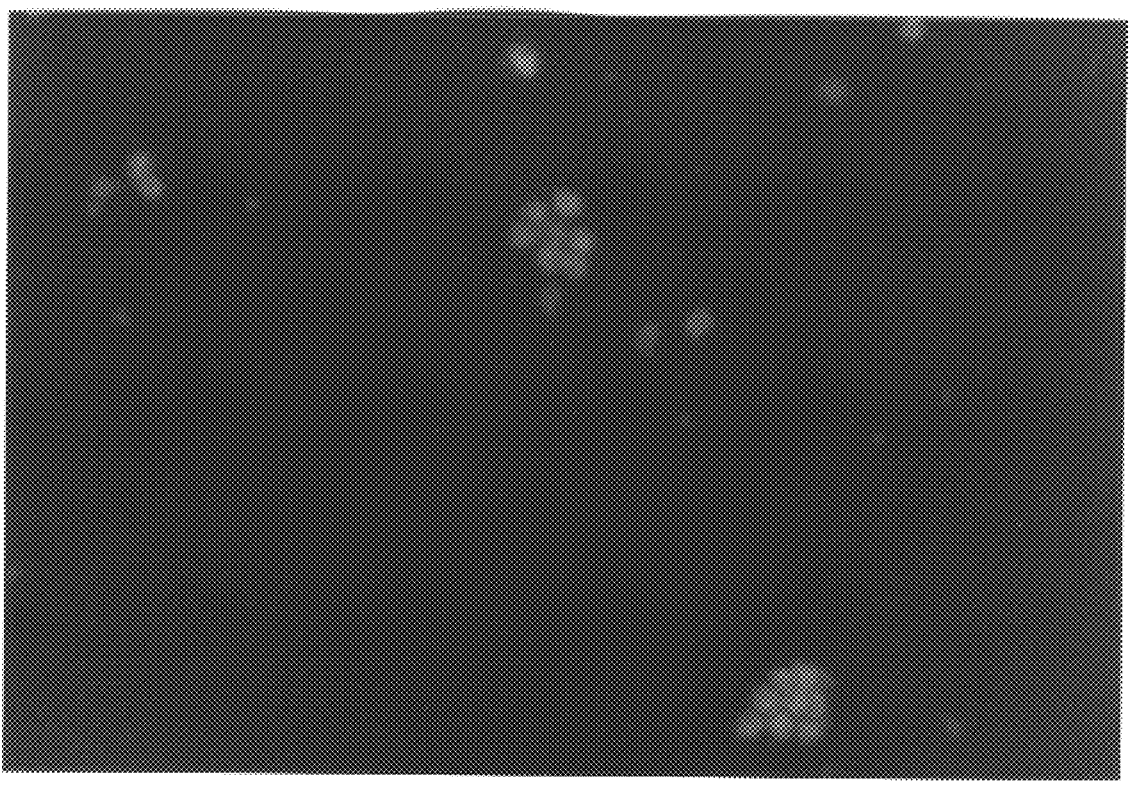
FIG. 21 is a photograph showing the indirect immunofluorescent staining of induced human monocytes with mouse IgG1 monoclonal antibody 2A12-A4 magnified 1600×.

The ability of the various monoclonal antibodies to bind to iNOS in cells that have been induced to produce iNOS was examined in three different cell types, A-172 a human glioblastoma cell line, RAW 264.7 a mouse macrophage cell line, and normal human monocytes. The cells were cultured for two (2) days in normal medium and then induced to produce iNOS by treatment for 40 hours with a cytokine/LPS mixture (CM). Following the treatment, the cells were processed in one of two ways, either for lysis or for immunostaining. The cells that were to be lysed were detached from the culture flask, washed five (5) times, and frozen in a small volume of PBS to lyse. These were used for western immunoblots and to test the sandwich ELISA described in Examples 5 and 6 hereinbefore. The cells for immunostaining were washed four (4) times, and fixed in either 70% or 100% acetone. They were reacted for 60 minutes with the primary mouse anti-hiNOS monoclonal antibody, and then with FITC-conjugated goat anti-mouse IgG or IgM. They were observed and photographed by epifluorescence microscopy. FIGS. 15–17 illustrate the indirect immunofluorescent staining pattern observed on induced A-172 cells with three (3) different mouse anti-hiNOS monoclonal antibodies, 1E8-B8, 2A12-A4, and 2H11-D11 of Table IV, respectively. FIGS. 18 and 19 illustrate the indirect immunofluorescent staining observed on the fixed RAW 264.7 cells with anti-hiNOS monoclonal antibodies, 1E8-B8 and 2A12-A4 of Table IV, respectively. This shows that these two monoclones will also recognize and bind to mouse iNOS. This is similar to the results found by western immunoblotting. That is to say, these two (2) monoclonals can cross react with mouse iNOS. FIGS. 20 and 21 show the indirect immunostaining achieved using two (2) mouse anti-hiNOS monoclonal antibodies, 1E8-B8 and 2A12-A4 of Table IV, respectively, on induced normal human monocytes. The monocytes were isolated from normal human blood by density gradient centrifugation using Optiprep obtained from Accurate Chemical and Scientific Corp, Westbury, N.Y., following the manufacturer's direction as delineated in Application Sheet 2.3. These results show that these mouse anti-hiNOS monoclonal antibodies can recognize and bind to hiNOS which has been induced in normal human cells and tissues.

EXAMPLE 8

TEST OF MONOCLONAL ANTIBODIES ABILITY TO INHIBIT THE ENZYMATIC ACTIVITY OF HINOS

The enzymatic activity of hiNOS was determined by measuring the amount of nitrite produced in the presence of the substrates and co-factors. We tested 13 different anti-hiNOS monoclonal antibodies for their ability to inhibit the activity of hiNOS. None of the monoclonal antibodies tested was found to inhibit the activity of the enzyme as determined by the Greise calorimetric assay described in an article entitled "Macrophage Deactivity Factor and Transforming Growth Factors—beta1, beta2, and beta3 Inhibit Induction of Macrophage Nitrogen Oxide Synthesis by IFN-gamma1" by Ding et al., Journal of Immunology, Vol. 145 (1990), and in an article entitled "Cloned Human Brain Nitric Oxide Synthase is Highly Expressed in Skeletal Muscle" by Nakane et al., FEBS Letters, Vol. 316 (1993).

What is claimed is:

1. Monoclonal antibodies specifically recognizing human iNOS enzyme without cross-reacting with human nNOS or human eNOS enzymes.

2. The monoclonal antibodies of claim 1 which consist of the isotypes mouse IgG or IgM.

3. An immunoassay method utilizing a monoclonal antibody reactive specifically to human INOS enzyme, without cross-reacting with human nNOS or human eNOS enzyme, in a sample comprising the steps of:
   a. contacting a sample of human iNOS enzyme with the monoclonal antibody; and
   b. detecting the presence of the human iNOS enzyme in the sample.

4. The method of claim 3 which additionally comprises the step of providing a substrate capable of binding anti-human iNOS antibodies, prior to said step of contacting the sample of human iNOS enzyme with the monoclonal antibody.

5. Monoclonal antibodies reognizing human iNOS enzyme of claim 1 which also bind to specific regions of human iNOS enzyme represented by the peptides of FIG. 1.

6. A peptide sequence used to epitope map monoclonal antibodies that recognize human iNOS wherein said peptide sequence is selected from the group consisting of the peptide sequences 1–5 of FIG. 1.

7. A peptide sequence used to epitope map monoclonal antibodies that recognize human iNOS, wherein said peptide sequence is selected from the group consisting of the peptide sequences 6–15 of FIG. 7A, 16–25 of FIG. 7B, 26–35 of FIG. 7C, and 36–45 of FIG. 7D.

8. A peptide sequence used to determine the specificity of recognition of human INOS by monoclonal antibodies, wherein said peptide sequence is selected from the group consisting of the peptide sequences 46–53 of FIG. 8.

9. Monoclonal antibodies elicited by human iNOS that specifically recognize human iNOS enzyme without cross-reacting with human nNOS or human eNOS enzymes.

* * * * *

SEQUENCE LISTING (1) GENERAL INFORMATION:

(iii) NUMBER OF SEQUENCES: 85

(2) INFORMATION FOR SEQ ID NO: 1:

(i) SEQUENCE CHARACTERISTICS:
        (A) LENGTH: 18
        (B) TYPE: AMINO ACID
        (D) TOPOLOGY: LINEAR (ii) MOLECULE TYPE: PEPTIDE (ix) FEATURE:
        (A) NAME/KEY: HUMAN iNOS (25-42)
        (B) LOCATION:
        (C) IDENTIFICATION METHOD: AMINO ACID ANALYSIS
        (D) OTHER INFORMATION:

(xi) SEQUENCE DESCRIPTION: SEQ ID NO: 1:

Asn  Asn  Asn  Val  Glu  Lys  Ala  Pro  Cys  Ala  Thr   Ser Ser
                    5                        10

Pro  Val  Thr  Gln  Asp
     15

(2) INFORMATION FOR SEQ ID NO: 2:

(i) SEQUENCE CHARACTERISTICS:
        (A) LENGTH: 18
        (B) TYPE: AMINO ACID
        (D) TOPOLOGY: LINEAR (ii) MOLECULE TYPE: PEPTIDE (ix) FEATURE:
        (A) NAME/KEY: MOUSE iNOS (25-42)
        (B) LOCATION:
        (C) IDENTIFICATION METHOD: AMINO ACID ANALYSIS
        (D) OTHER INFORMATION:

(xi) SEQUENCE DESCRIPTION: SEQ ID NO: 2:

Asn  Asn  Asn  Val  Lys  Lys  Thr  Pro  Cys  Ala  Val   Leu Ser
1                   5                        10

Pro  Thr  Ile  Gln  Asp
     15

(2) INFORMATION FOR SEQ ID NO: 3:

(i) SEQUENCE CHARACTERISTICS:
        (A) LENGTH: 18
        (B) TYPE: AMINO ACID
        (D) TOPOLOGY: LINEAR (ii) MOLECULE TYPE: PEPTIDE (ix) FEATURE:
        (A) NAME/KEY: RAT iNOS (25-42)
        (B) LOCATION:
        (C) IDENTIFICATION METHOD: AMINO ACID ANALYSIS
        (D) OTHER INFORMATION:

(xi) SEQUENCE DESCRIPTION: SEQ ID NO: 3:

Asn  Asn  Asn  Val  Glu  Lys  Thr  Pro  Gly  Ala  Ile   Pro Ser
                    5                        10

Pro  Thr  Thr  Gln  Asp
     15

(2) INFORMATION FOR SEQ ID NO: 4:

(i) SEQUENCE CHARACTERISTICS:
        (A) LENGTH: 18
        (B) TYPE: AMINO ACID
        (D) TOPOLOGY: LINEAR (ii) MOLECULE TYPE: PEPTIDE (ix) FEATURE:
        (A) NAME/KEY: HUMAN iNOS (37-54)
        (B) LOCATION:
        (C) IDENTIFICATION METHOD: AMINO ACID ANALYSIS
        (D) OTHER INFORMATION:

(xi) SEQUENCE DESCRIPTION: SEQ ID NO: 4:

Ser  Pro  Val  Thr  Gln  Asp  Asp  Leu  Gln  Tyr  His  Asn  Leu
                    5                        10

Ser  Lys  Gln  Gln  Asn
     15

(2) INFORMATION FOR SEQ ID NO: 5:

(i) SEQUENCE CHARACTERISTICS:
        (A) LENGTH: 18
        (B) TYPE: AMINO ACID
        (D) TOPOLOGY: LINEAR (ii) MOLECULE TYPE: PEPTIDE (ix) FEATURE:
        (A) NAME/KEY: HUMAN iNOS (781-798)
        (B) LOCATION:
        (C) IDENTIFICATION METHOD: AMINO ACID ANALYSIS
        (D) OTHER INFORMATION:

(xi) SEQUENCE DESCRIPTION: SEQ ID NO: 5:

Pro  Ala  Leu  Val  Gln  Gly  Ile  Leu  Glu  Arg  Val  Val  Asp
                    5                        10

Gly  Pro  Thr  Pro  His
     15

(2) INFORMATION FOR SEQ ID NO: 6:

(i) SEQUENCE CHARACTERISTICS:
        (A) LENGTH: 18
        (B) TYPE: AMINO ACID
        (D) TOPOLOGY: LINEAR (ii) MOLECULE TYPE: PEPTIDE (ix) FEATURE:
        (A) NAME/KEY: MOUSE iNOS (776-792)
        (B) LOCATION:
        (C) IDENTIFICATION METHOD: AMINO ACID ANALYSIS
        (D) OTHER INFORMATION:

(xi) SEQUENCE DESCRIPTION: SEQ ID NO: 6:

Xaa  Ala  Leu  Val  Gln  Gly  Ile  Leu  Glu  Arg  Val  Val  Asp
                    5                        10

Cys  Pro  Thr  Pro  His
     15

(2) INFORMATION FOR SEQ ID NO: 7:

(i) SEQUENCE CHARACTERISTICS:
        (A) LENGTH: 18
        (B) TYPE: AMINO ACID
        (D) TOPOLOGY: LINEAR (ii) MOLECULE TYPE: PEPTIDE (ix) FEATURE:
    (A) NAME/KEY: RAT iNOS (780-794)
    (B) LOCATION:
    (C) IDENTIFICATION METHOD: AMINO ACID ANALYSIS
    (D) OTHER INFORMATION:

(xi) SEQUENCE DESCRIPTION: SEQ ID NO: 7:

Xaa Xaa Leu Val Gln Gly Ile Leu Glu Arg Val Val Asp
1           5                   10

Cys Ser Ser Pro Xaa
            15

(2) INFORMATION FOR SEQ ID NO: 8:

(i) SEQUENCE CHARACTERISTICS:
        (A) LENGTH: 18
        (B) TYPE: AMINO ACID
        (D) TOPOLOGY: LINEAR (ii) MOLECULE TYPE: PEPTIDE (ix) FEATURE:
        (A) NAME/KEY: HUMAN iNOS (985-1002)
        (B) LOCATION:
        (C) IDENTIFICATION METHOD: AMINO ACID ANALYSIS
        (D) OTHER INFORMATION:

(xi) SEQUENCE DESCRIPTION: SEQ ID NO: 8:

Gly Ile Val Pro Phe Arg Ser Phe Trp Gln Gln Arg Leu
                5                   10

His Asp Ser Gln His
            15

(2) INFORMATION FOR SEQ ID NO: 9:

(i) SEQUENCE CHARACTERISTICS:
        (A) LENGTH: 18
        (B) TYPE: AMINO ACID
        (D) TOPOLOGY: LINEAR (ii) MOLECULE TYPE: PEPTIDE (ix) FEATURE:
        (A) NAME/KEY: MOUSE iNOS (978-995)
        (B) LOCATION:
        (C) IDENTIFICATION METHOD: AMINO ACID ANALYSIS
        (D) OTHER INFORMATION:

(xi) SEQUENCE DESCRIPTION: SEQ ID NO: 9:

Gly Ile Ala Pro Phe Arg Ser Phe Trp Gln Gln Arg Leu
                5                   10

His Asp Ser Gln His
            15

(2) INFORMATION FOR SEQ ID NO: 10:

(i) SEQUENCE CHARACTERISTICS:
        (A) LENGTH: 18
        (B) TYPE: AMINO ACID
        (D) TOPOLOGY: LINEAR (ii) MOLECULE TYPE: PEPTIDE (ix) FEATURE:
        (A) NAME/KEY: RAT iNOS (982-998)
        (B) LOCATION:
        (C) IDENTIFICATION METHOD: AMINO ACID ANALYSIS (D) OTHER INFORMATION:

(xi) SEQUENCE DESCRIPTION: SEQ ID NO: 10:

Gly Ile Ala Pro Phe Arg Ser Phe Trp Gln Gln Arg Leu
                      5                   10

His Asp Ser Gln His
      15

(2) INFORMATION FOR SEQ ID NO: 11:

(i) SEQUENCE CHARACTERISTICS:
        (A) LENGTH: 18
        (B) TYPE: AMINO ACID
        (D) TOPOLOGY: LINEAR (ii) MOLECULE TYPE: PEPTIDE (ix) FEATURE:
        (A) NAME/KEY: HUMAN nNOS (1256-1273)
        (B) LOCATION:
        (C) IDENTIFICATION METHOD: AMINO ACID ANALYSIS
        (D) OTHER INFORMATION:

(xi) SEQUENCE DESCRIPTION: SEQ ID NO: 11:

Gly Ile Ala Pro Phe Arg Ser Phe Trp Gln Gln Arg Gln
                      5                   10

Phe Asp Ile Gln His
      15

(2) INFORMATION FOR SEQ ID NO: 12:

(i) SEQUENCE CHARACTERISTICS:
        (A) LENGTH: 18
        (B) TYPE: AMINO ACID
        (D) TOPOLOGY: LINEAR (ii) MOLECULE TYPE: PEPTIDE (ix) FEATURE:
        (A) NAME/KEY: HUMAN eNOS (1017-1031)
        (B) LOCATION:
        (C) IDENTIFICATION METHOD: AMINO ACID ANALYSIS
        (D) OTHER INFORMATION:

(xi) SEQUENCE DESCRIPTION: SEQ ID NO: 12:

Gly Ile Ala Pro Phe Arg Gly Phe Trp Gln Glu Arg Leu
                      5                   10

His Asp Xaa Xaa Xaa
      15

(2) INFORMATION FOR SEQ ID NO: 13:

(i) SEQUENCE CHARACTERISTICS:
        (A) LENGTH: 18
        (B) TYPE: AMINO ACID
        (D) TOPOLOGY: LINEAR (ii) MOLECULE TYPE: PEPTIDE (ix) FEATURE:
        (A) NAME/KEY: BOVINE eNOS (1019-1033)
        (B) LOCATION:
        (C) IDENTIFICATION METHOD: AMINO ACID ANALYSIS
        (D) OTHER INFORMATION:

(xi) SEQUENCE DESCRIPTION: SEQ ID NO: 13:

Gly Ile Ala Pro Phe Arg Gly Phe Trp Gln Glu Arg Leu
                      5                   10

```
His Asp Xaa Xaa Xaa
    15

(2) INFORMATION FOR SEQ ID NO: 14:

(i) SEQUENCE CHARACTERISTICS:
        (A) LENGTH: 18
        (B) TYPE: AMINO ACID
        (D) TOPOLOGY: LINEAR (ii) MOLECULE TYPE: PEPTIDE (ix) FEATURE:
        (A) NAME/KEY: HUMAN iNOS (1009-1026)
        (B) LOCATION:
        (C) IDENTIFICATION METHOD: AMINO ACID ANALYSIS
        (D) OTHER INFORMATION:

(xi) SEQUENCE DESCRIPTION: SEQ ID NO: 14:

Arg Met Thr Leu Val Phe Gly Cys Arg Arg Pro Asp Glu
                5                   10

Asp His Ile Tyr Gln
    15

(2) INFORMATION FOR SEQ ID NO: 15:

(i) SEQUENCE CHARACTERISTICS:
        (A) LENGTH: 18
        (B) TYPE: AMINO ACID
        (D) TOPOLOGY: LINEAR (ii) MOLECULE TYPE: PEPTIDE (ix) FEATURE:
        (A) NAME/KEY: RAT iNOS (1006-1023)
        (B) LOCATION:
        (C) IDENTIFICATION METHOD: AMINO ACID ANALYSIS
        (D) OTHER INFORMATION:

(xi) SEQUENCE DESCRIPTION: SEQ ID NO: 15:

Arg Met Thr Leu Val Phe Gly Cys Arg His Pro Glu Glu
                5                   10

Asp His Leu Tyr Gln
    15

(2) INFORMATION FOR SEQ ID NO: 16:

(i) SEQUENCE CHARACTERISTICS:
        (A) LENGTH: 18
        (B) TYPE: AMINO ACID
        (D) TOPOLOGY: LINEAR (ii) MOLECULE TYPE: PEPTIDE (ix) FEATURE:
        (A) NAME/KEY: MOUSE iNOS (1002-1019)
        (B) LOCATION:
        (C) IDENTIFICATION METHOD: AMINO ACID ANALYSIS
        (D) OTHER INFORMATION:

(xi) SEQUENCE DESCRIPTION: SEQ ID NO: 16:

Arg Met Ser Leu Val Phe Gly Cys Arg His Pro Glu Glu
                5                   10

Asp His Leu Tyr Gln
    15

(2) INFORMATION FOR SEQ ID NO: 17:

(i) SEQUENCE CHARACTERISTICS:
```

(A) LENGTH: 16
         (B) TYPE: AMINO ACID
         (D) TOPOLOGY: LINEAR (ii) MOLECULE TYPE: PEPTIDE (ix) FEATURE:
         (A) NAME/KEY: hnNOS [2-16, Cys17]
         (B) LOCATION: HUMAN nNOS: AMINO TERMINAL
         (C) IDENTIFICATION METHOD: AMINO ACID ANALYSIS
         (D) OTHER INFORMATION:

(xi) SEQUENCE DESCRIPTION: SEQ ID NO: 17:

Glu  Asp  His  Met  Phe  Gly  Val  Gln  Gln  Ile  Gln  Pro  Asn
                    5                        10

Val  Ile  Cys
          15

(2) INFORMATION FOR SEQ ID NO: 18:

(i) SEQUENCE CHARACTERISTICS:
        (A) LENGTH: 24
        (B) TYPE: AMINO ACID
        (D) TOPOLOGY: LINEAR (ii) MOLECULE TYPE: PEPTIDE (ix) FEATURE:
         (A) NAME/KEY: hnNOS [Cys1410-1411-1433]
         (B) LOCATION: HUMAN nNOS: CARBOXYL TERMINAL
         (C) IDENTIFICATION METHOD: AMINO ACID ANALYSIS
         (D) OTHER INFORMATION:

(xi) SEQUENCE DESCRIPTION: SEQ ID NO: 18:

Cys  Arg  Leu  Arg  Ser  Glu  Ser  Ile  Ala  Phe  Ile  Glu  Glu
                    5                        10

Ser  Lys  Lys  Asp  Thr  Asp  Glu  Val  Phe  Ser  Ser
          15                  20

(2) INFORMATION FOR SEQ ID NO: 19:

(i) SEQUENCE CHARACTERISTICS:
        (A) LENGTH: 20
        (B) TYPE: AMINO ACID
        (D) TOPOLOGY: LINEAR (ii) MOLECULE TYPE: PEPTIDE (ix) FEATURE:
         (A) NAME/KEY: hiNOS [2-21, Ser2]
         (B) LOCATION: HUMAN iNOS: AMINO TERMINAL
         (C) IDENTIFICATION METHOD: AMINO ACID ANALYSIS
         (D) OTHER INFORMATION:

(xi) SEQUENCE DESCRIPTION: SEQ ID NO: 19:

Ala  Ser  Pro  Trp  Lys  Phe  Leu  Phe  Lys  Thr  Lys  Phe  His
                    5                        10

Gln  Tyr  Ala  Met  Asn  Gly  Glu
          15                  20

(2) INFORMATION FOR SEQ ID NO: 20:

(i) SEQUENCE CHARACTERISTICS:
        (A) LENGTH: 18
        (B) TYPE: AMINO ACID
        (D) TOPOLOGY: LINEAR (ii) MOLECULE TYPE: PEPTIDE (ix) FEATURE:

(A) NAME/KEY: hiNOS [Cys1136-1137-1153]
        (B) LOCATION: HUMAN iNOS: CARBOXYL TERMINAL
        (C) IDENTIFICATION METHOD: AMINO ACID ANALYSIS
        (D) OTHER INFORMATION:

(xi) SEQUENCE DESCRIPTION: SEQ ID NO: 20:

Cys Lys Lys Asp Arg Val Ala Val Gln Pro Ser Ser Leu
                  5                  10

Glu Met Ser Ala Leu
 15

(2) INFORMATION FOR SEQ ID NO: 21:

(i) SEQUENCE CHARACTERISTICS:
        (A) LENGTH: 12
        (B) TYPE: AMINO ACID
        (D) TOPOLOGY: LINEAR (ii) MOLECULE TYPE: PEPTIDE (ix) FEATURE:
        (A) NAME/KEY: heNOS [Cap-2-12, Cys13]
        (B) LOCATION: HUMAN eNOS: AMINO TERMINAL WITH CAPROIC
            ACID                     ATTACHED
        (C) IDENTIFICATION METHOD: AMINO ACID ANALYSIS
        (D) OTHER INFORMATION:

(xi) SEQUENCE DESCRIPTION: SEQ ID NO: 21:

Gly Asn Leu Lys Ser Val Ala Gln Glu Pro Gly Cys
                  5                  10

(2) INFORMATION FOR SEQ ID NO: 22:

(i) SEQUENCE CHARACTERISTICS:
        (A) LENGTH: 12
        (B) TYPE: AMINO ACID
        (D) TOPOLOGY: LINEAR (ii) MOLECULE TYPE: PEPTIDE (ix) FEATURE:
        (A) NAME/KEY: heNOS [2-12, Cys13]
        (B) LOCATION: HUMAN eNOS: AMINO TERMINAL WITHOUT
            CAPROIC ACID             ATTACHED
        (C) IDENTIFICATION METHOD: AMINO ACID ANALYSIS
        (D) OTHER INFORMATION:

(xi) SEQUENCE DESCRIPTION: SEQ ID NO: 22:

Gly Asn Leu Lys Ser Val Ala Gln Glu Pro Gly Cys
                  5                  10

(2) INFORMATION FOR SEQ ID NO: 23:

(i) SEQUENCE CHARACTERISTICS:
        (A) LENGTH: 23
        (B) TYPE: AMINO ACID
        (D) TOPOLOGY: LINEAR (ii) MOLECULE TYPE: PEPTIDE (ix) FEATURE:
        (A) NAME/KEY: heNOS [Cys1181-1182-1203]
        (B) LOCATION: HUMAN eNOS: CARBOXYL TERMINAL
        (C) IDENTIFICATION METHOD: AMINO ACID ANALYSIS
        (D) OTHER INFORMATION:

(xi) SEQUENCE DESCRIPTION: SEQ ID NO: 23:

Cys Glu Arg Gln Leu Arg Glu Ala Val Pro Trp Ala Phe
                  5                  10

Asp Pro Pro Gly Ser Asp Thr Asn Ser Pro 15                    20

(2) INFORMATION FOR SEQ ID NO: 24:

(i) SEQUENCE CHARACTERISTICS:
        (A) LENGTH: 18
        (B) TYPE: AMINO ACID
        (D) TOPOLOGY: LINEAR (ii) MOLECULE TYPE: PEPTIDE (ix) FEATURE:
        (A) NAME/KEY: hiNOS [985-1002]
        (B) LOCATION:
        (C) IDENTIFICATION METHOD: AMINO ACID ANALYSIS
        (D) OTHER INFORMATION:

(xi) SEQUENCE DESCRIPTION: SEQ ID NO: 24:

Gly  Ile  Val  Pro  Phe  Arg  Ser  Phe  Trp  Gln  Gln  Arg  Leu
                         5                        10

His  Asp  Ser  Gln  His
               15

(2) INFORMATION FOR SEQ ID NO: 25:

(i) SEQUENCE CHARACTERISTICS:
        (A) LENGTH: 18
        (B) TYPE: AMINO ACID
        (D) TOPOLOGY: LINEAR (ii) MOLECULE TYPE: PEPTIDE (ix) FEATURE:
        (A) NAME/KEY: hiNOS [985-1002]
        (B) LOCATION:
        (C) IDENTIFICATION METHOD: AMINO ACID ANALYSIS
        (D) OTHER INFORMATION:

(xi) SEQUENCE DESCRIPTION: SEQ ID NO: 25:

Gly  Ile  Val  Pro  Phe  Arg  Ser  Phe  Trp  Gln  Gln  Arg  Leu
                         5                        10

His  Asp  Ser  Gln  His
               15

(2) INFORMATION FOR SEQ ID NO: 26:

(i) SEQUENCE CHARACTERISTICS:
        (A) LENGTH: 18
        (B) TYPE: AMINO ACID
        (D) TOPOLOGY: LINEAR (ii) MOLECULE TYPE: PEPTIDE (ix) FEATURE:
        (A) NAME/KEY: hiNOS [37-54]
        (B) LOCATION:
        (C) IDENTIFICATION METHOD: AMINO ACID ANALYSIS
        (D) OTHER INFORMATION:

(xi) SEQUENCE DESCRIPTION: SEQ ID NO: 26:

Ser  Pro  Val  Thr  Gln  Asp  Asp  Leu  Gln  Tyr  His  Asn  Leu
                         5                        10

Ser  Lys  Gln  Gln  Asn
               15

(2) INFORMATION FOR SEQ ID NO: 27:

(i) SEQUENCE CHARACTERISTICS:
        (A) LENGTH: 18

```
        (B) TYPE: AMINO ACID
        (D) TOPOLOGY: LINEAR (ii) MOLECULE TYPE: PEPTIDE (ix) FEATURE:
        (A) NAME/KEY: hiNOS [781-798]
        (B) LOCATION:
        (C) IDENTIFICATION METHOD: AMINO ACID ANALYSIS
        (D) OTHER INFORMATION:

(xi) SEQUENCE DESCRIPTION: SEQ ID NO: 27:

Pro  Ala  Leu  Val  Gln  Gly  Ile  Leu  Glu  Arg  Val  Val  Asp
                    5                        10

Gly  Pro  Thr  Pro  His
              15

(2) INFORMATION FOR SEQ ID NO: 28:

(i) SEQUENCE CHARACTERISTICS:
        (A) LENGTH: 18
        (B) TYPE: AMINO ACID
        (D) TOPOLOGY: LINEAR (ii) MOLECULE TYPE: PEPTIDE (ix) FEATURE:
        (A) NAME/KEY: hiNOS [25-42]
        (B) LOCATION:
        (C) IDENTIFICATION METHOD: AMINO ACID ANALYSIS
        (D) OTHER INFORMATION:

(xi) SEQUENCE DESCRIPTION: SEQ ID NO: 28:

Asn  Asn  Asn  Val  Glu  Lys  Ala  Pro  Ser  Ala  Thr  Ser  Ser
                    5                        10

Pro  Val  Thr  Gln  Asp
              15

(2) INFORMATION FOR SEQ ID NO: 29:

(i) SEQUENCE CHARACTERISTICS:
        (A) LENGTH: 18
        (B) TYPE: AMINO ACID
        (D) TOPOLOGY: LINEAR (ii) MOLECULE TYPE: PEPTIDE (ix) FEATURE:
        (A) NAME/KEY: hiNOS [37-54]
        (B) LOCATION:
        (C) IDENTIFICATION METHOD: AMINO ACID ANALYSIS
        (D) OTHER INFORMATION:

(xi) SEQUENCE DESCRIPTION: SEQ ID NO: 29:

Ser  Pro  Val  Thr  Gln  Asp  Asp  Leu  Gln  Tyr  His  Asn  Leu
                    5                        10

Ser  Lys  Gln  Gln  Asn
              15

(2) INFORMATION FOR SEQ ID NO: 30:

(i) SEQUENCE CHARACTERISTICS:
        (A) LENGTH: 18
        (B) TYPE: AMINO ACID
        (D) TOPOLOGY: LINEAR (ii) MOLECULE TYPE: PEPTIDE (ix) FEATURE:
        (A) NAME/KEY: hiNOS [781-798]
```

-continued

```
        (B) LOCATION:
        (C) IDENTIFICATION METHOD: AMINO ACID ANALYSIS
        (D) OTHER INFORMATION:

(xi) SEQUENCE DESCRIPTION: SEQ ID NO: 30:

Pro  Ala  Leu  Val  Gln  Gly  Ile  Leu  Glu  Arg  Val  Val  Asp
                       5                        10
Gly  Pro  Thr  Pro  His
     15

(2) INFORMATION FOR SEQ ID NO: 31:

(i) SEQUENCE CHARACTERISTICS:
        (A) LENGTH: 18
        (B) TYPE: AMINO ACID
        (D) TOPOLOGY: LINEAR (ii) MOLECULE TYPE: PEPTIDE (ix) FEATURE:
        (A) NAME/KEY: hiNOS [1009-1026]
        (B) LOCATION:
        (C) IDENTIFICATION METHOD: AMINO ACID ANALYSIS
        (D) OTHER INFORMATION:

(xi) SEQUENCE DESCRIPTION: SEQ ID NO: 31:

Arg  Met  Thr  Leu  Val  Phe  Gly  Ser  Arg  Arg  Pro  Asp  Glu
                       5                        10
Asp  His  Ile  Tyr  Gln
     15

(2) INFORMATION FOR SEQ ID NO: 32:

(i) SEQUENCE CHARACTERISTICS:
        (A) LENGTH: 18
        (B) TYPE: AMINO ACID
        (D) TOPOLOGY: LINEAR (ii) MOLECULE TYPE: PEPTIDE (ix) FEATURE:
        (A) NAME/KEY: (A3) LOCUS HUMAN iNOS (25-42)
        (B) LOCATION: CARBOXY TERMINAL WITH AMIDE
        (C) IDENTIFICATION METHOD: AMINO ACID ANALYSIS
        (D) OTHER INFORMATION:

(xi) SEQUENCE DESCRIPTION: SEQ ID NO: 32:

Asn  Asn  Asn  Val  Glu  Lys  Ala  Pro  Ser  Ala  Thr  Ser  Ser
                       5                        10
Pro  Val  Thr  Gln  Asp
     15

(2) INFORMATION FOR SEQ ID NO: 33:

(i) SEQUENCE CHARACTERISTICS:
        (A) LENGTH: 18
        (B) TYPE: AMINO ACID
        (D) TOPOLOGY: LINEAR (ii) MOLECULE TYPE: PEPTIDE (ix) FEATURE:
        (A) NAME/KEY: MOUSE iNOS (25-42)
        (B) LOCATION: CARBOXY TERMINAL WITH AMIDE
        (C) IDENTIFICATION METHOD: AMINO ACID ANALYSIS
        (D) OTHER INFORMATION:

(xi) SEQUENCE DESCRIPTION: SEQ ID NO: 33:

Asn  Asn  Asn  Val  Lys  Lys  Thr  Pro  Ser  Ala  Val  Leu  Ser
```

```
                      5                  10
Pro Thr Ile Gln Asp
             15
```

(2) INFORMATION FOR SEQ ID NO: 34:

(i) SEQUENCE CHARACTERISTICS:
        (A) LENGTH: 18
        (B) TYPE: AMINO ACID
        (D) TOPOLOGY: LINEAR (ii) MOLECULE TYPE: PEPTIDE (ix) FEATURE:
        (A) NAME/KEY: RAT iNOS (25-42)
        (B) LOCATION: CARBOXY TERMINAL WITH AMIDE
        (C) IDENTIFICATION METHOD: AMINO ACID ANALYSIS
        (D) OTHER INFORMATION:

(xi) SEQUENCE DESCRIPTION: SEQ ID NO: 34:

```
Asn Asn Asn Val Glu Lys Thr Pro Gly Ala Ile Pro Ser
                 5                  10
Pro Thr Thr Gln Asp
             15
```

(2) INFORMATION FOR SEQ ID NO: 35:

(i) SEQUENCE CHARACTERISTICS:
        (A) LENGTH: 15
        (B) TYPE: AMINO ACID
        (D) TOPOLOGY: LINEAR (ii) MOLECULE TYPE: PEPTIDE (ix) FEATURE:
        (A) NAME/KEY: HUMAN iNOS (28-42)
        (B) LOCATION: CARBOXY TERMINAL WITH AMIDE
        (C) IDENTIFICATION METHOD: AMINO ACID ANALYSIS
        (D) OTHER INFORMATION:

(xi) SEQUENCE DESCRIPTION: SEQ ID NO: 35:

```
Val Glu Lys Ala Pro Ser Ala Thr Ser Ser Pro Val Thr
                 5                  10
Gln Asp
    15
```

(2) INFORMATION FOR SEQ ID NO: 36:

(i) SEQUENCE CHARACTERISTICS:
        (A) LENGTH: 12
        (B) TYPE: AMINO ACID
        (D) TOPOLOGY: LINEAR (ii) MOLECULE TYPE: PEPTIDE (ix) FEATURE:
        (A) NAME/KEY: HUMAN iNOS (31-42)
        (B) LOCATION: CARBOXY TERMINAL WITH AMIDE
        (C) IDENTIFICATION METHOD: AMINO ACID ANALYSIS
        (D) OTHER INFORMATION:

(xi) SEQUENCE DESCRIPTION: SEQ ID NO: 36:

```
Ala Pro Ser Ala Thr Ser Ser Pro Val Thr Gln Asp
                 5                  10
```

(2) INFORMATION FOR SEQ ID NO: 37:

(i) SEQUENCE CHARACTERISTICS:
        (A) LENGTH: 9

(B) TYPE: AMINO ACID
            (D) TOPOLOGY: LINEAR (ii) MOLECULE TYPE: PEPTIDE (ix) FEATURE:
            (A) NAME/KEY: HUMAN iNOS (34-42)
            (B) LOCATION: CARBOXY TERMINAL WITH AMIDE
            (C) IDENTIFICATION METHOD: AMINO ACID ANALYSIS
            (D) OTHER INFORMATION:

(xi) SEQUENCE DESCRIPTION: SEQ ID NO: 37:

Ala  Thr  Ser  Ser  Pro  Val  Thr  Gln  Asp
                     5

(2) INFORMATION FOR SEQ ID NO: 38:

(i) SEQUENCE CHARACTERISTICS:
            (A) LENGTH: 6
            (B) TYPE: AMINO ACID
            (D) TOPOLOGY: LINEAR (ii) MOLECULE TYPE: PEPTIDE (ix) FEATURE:
            (A) NAME/KEY: HUMAN iNOS (37-42)
            (B) LOCATION: CARBOXY TERMINAL WITH AMIDE
            (C) IDENTIFICATION METHOD: AMINO ACID ANALYSIS
            (D) OTHER INFORMATION:

(xi) SEQUENCE DESCRIPTION: SEQ ID NO: 38:

Ser  Pro  Val  Thr  Gln  Asp
                     5

(2) INFORMATION FOR SEQ ID NO: 39:

(i) SEQUENCE CHARACTERISTICS:
            (A) LENGTH: 15
            (B) TYPE: AMINO ACID
            (D) TOPOLOGY: LINEAR (ii) MOLECULE TYPE: PEPTIDE (ix) FEATURE:
            (A) NAME/KEY: HUMAN iNOS (25-39)
            (B) LOCATION: CARBOXY TERMINAL WITH AMIDE
            (C) IDENTIFICATION METHOD: AMINO ACID ANALYSIS
            (D) OTHER INFORMATION:

(xi) SEQUENCE DESCRIPTION: SEQ ID NO: 39:

Asn  Asn  Asn  Val  Glu  Lys  Ala  Pro  Ser  Ala  Thr  Ser  Ser
                     5                        10

Pro  Val
     15

(2) INFORMATION FOR SEQ ID NO: 40:

(i) SEQUENCE CHARACTERISTICS:
            (A) LENGTH: 12
            (B) TYPE: AMINO ACID
            (D) TOPOLOGY: LINEAR (ii) MOLECULE TYPE: PEPTIDE (ix) FEATURE:
            (A) NAME/KEY: HUMAN iNOS (25-36)
            (B) LOCATION: CARBOXY TERMINAL WITH AMIDE
            (C) IDENTIFICATION METHOD: AMINO ACID ANALYSIS
            (D) OTHER INFORMATION:

(xi) SEQUENCE DESCRIPTION: SEQ ID NO: 40:

Asn Asn Asn Val Glu Lys Ala Pro Ser Ala Thr Ser
              5                   10

(2) INFORMATION FOR SEQ ID NO: 41:

(i) SEQUENCE CHARACTERISTICS:
        (A) LENGTH: 9
        (B) TYPE: AMINO ACID
        (D) TOPOLOGY: LINEAR (ii) MOLECULE TYPE: PEPTIDE (ix) FEATURE:
        (A) NAME/KEY: HUMAN iNOS (25-33)
        (B) LOCATION: CARBOXY TERMINAL WITH AMIDE
        (C) IDENTIFICATION METHOD: AMINO ACID ANALYSIS
        (D) OTHER INFORMATION:

(xi) SEQUENCE DESCRIPTION: SEQ ID NO: 41:

Asn Asn Asn Val Glu Lys Ala Pro Ser
              5

(2) INFORMATION FOR SEQ ID NO: 42:

(i) SEQUENCE CHARACTERISTICS:
        (A) LENGTH: 6
        (B) TYPE: AMINO ACID
        (D) TOPOLOGY: LINEAR (ii) MOLECULE TYPE: PEPTIDE (ix) FEATURE:
        (A) NAME/KEY: HUMAN iNOS (25-30)
        (B) LOCATION: CARBOXY TERMINAL WITH AMIDE
        (C) IDENTIFICATION METHOD: AMINO ACID ANALYSIS
        (D) OTHER INFORMATION:

(xi) SEQUENCE DESCRIPTION: SEQ ID NO: 42:

Asn Asn Asn Val Glu Lys
              5

(2) INFORMATION FOR SEQ ID NO: 43:

(i) SEQUENCE CHARACTERISTICS:
        (A) LENGTH: 18
        (B) TYPE: AMINO ACID
        (D) TOPOLOGY: LINEAR (ii) MOLECULE TYPE: PEPTIDE (ix) FEATURE:
        (A) NAME/KEY: (A4) LOCUS HUMAN iNOS (37-54)
        (B) LOCATION: CARBOXY TERMINAL WITH AMIDE
        (C) IDENTIFICATION METHOD: AMINO ACID ANALYSIS
        (D) OTHER INFORMATION:

(xi) SEQUENCE DESCRIPTION: SEQ ID NO: 43:

Ser Pro Val Thr Gln Asp Asp Leu Gln Tyr His Asn Leu
              5                   10

Ser Lys Gln Gln Asn
        15

(2) INFORMATION FOR SEQ ID NO: 44:

(i) SEQUENCE CHARACTERISTICS:
        (A) LENGTH: 15
        (B) TYPE: AMINO ACID
        (D) TOPOLOGY: LINEAR (ii) MOLECULE TYPE: PEPTIDE

```
        (ix) FEATURE:
              (A) NAME/KEY: HUMAN iNOS (40-54)
              (B) LOCATION: CARBOXY TERMINAL WITH AMIDE
              (C) IDENTIFICATION METHOD: AMINO ACID ANALYSIS
              (D) OTHER INFORMATION:

(xi) SEQUENCE DESCRIPTION: SEQ ID NO: 44:

Thr   Gln   Asp   Asp   Leu   Gln   Tyr   His   Asn   Leu   Ser   Lys   Gln
                        5                             10

Gln   Asn
      15

(2) INFORMATION FOR SEQ ID NO: 45:

(i) SEQUENCE CHARACTERISTICS:
              (A) LENGTH: 12
              (B) TYPE: AMINO ACID
              (D) TOPOLOGY: LINEAR (ii) MOLECULE TYPE: PEPTIDE (ix) FEATURE:
              (A) NAME/KEY: HUMAN iNOS (43-54)
              (B) LOCATION: CARBOXY TERMINAL WITH AMIDE
              (C) IDENTIFICATION METHOD: AMINO ACID ANALYSIS
              (D) OTHER INFORMATION:

(xi) SEQUENCE DESCRIPTION: SEQ ID NO: 45:

Asp   Leu   Gln   Tyr   His   Asn   Leu   Ser   Lys   Gln   Gln   Asn
                        5                             10

(2) INFORMATION FOR SEQ ID NO: 46:

(i) SEQUENCE CHARACTERISTICS:
              (A) LENGTH: 9
              (B) TYPE: AMINO ACID
              (D) TOPOLOGY: LINEAR (ii) MOLECULE TYPE: PEPTIDE (ix) FEATURE:
              (A) NAME/KEY: HUMAN iNOS (46-54)
              (B) LOCATION: CARBOXY TERMINAL WITH AMIDE
              (C) IDENTIFICATION METHOD: AMINO ACID ANALYSIS
              (D) OTHER INFORMATION:

(xi) SEQUENCE DESCRIPTION: SEQ ID NO: 46:

Tyr   His   Asn   Leu   Ser   Lys   Gln   Gln   Asn
                        5

(2) INFORMATION FOR SEQ ID NO: 47:

(i) SEQUENCE CHARACTERISTICS:
              (A) LENGTH: 6
              (B) TYPE: AMINO ACID
              (D) TOPOLOGY: LINEAR (ii) MOLECULE TYPE: PEPTIDE (ix) FEATURE:
              (A) NAME/KEY: HUMAN iNOS (49-54)
              (B) LOCATION: CARBOXY TERMINAL WITH AMIDE
              (C) IDENTIFICATION METHOD: AMINO ACID ANALYSIS
              (D) OTHER INFORMATION:

(xi) SEQUENCE DESCRIPTION: SEQ ID NO: 47:

Leu   Ser   Lys   Gln   Gln   Asn
                        5

(2) INFORMATION FOR SEQ ID NO: 48:
```

(i) SEQUENCE CHARACTERISTICS:
    (A) LENGTH: 15
    (B) TYPE: AMINO ACID
    (D) TOPOLOGY: LINEAR (ii) MOLECULE TYPE: PEPTIDE (ix) FEATURE:
    (A) NAME/KEY: HUMAN iNOS (37-51)
    (B) LOCATION: CARBOXY TERMINAL WITH AMIDE
    (C) IDENTIFICATION METHOD: AMINO ACID ANALYSIS
    (D) OTHER INFORMATION:

(xi) SEQUENCE DESCRIPTION: SEQ ID NO: 48:

Ser Pro Val Thr Gln Asp Asp Leu Gln Tyr His Asn Leu
                 5                   10
Ser Lys
    15

(2) INFORMATION FOR SEQ ID NO: 49:

(i) SEQUENCE CHARACTERISTICS:
        (A) LENGTH: 12
        (B) TYPE: AMINO ACID
        (D) TOPOLOGY: LINEAR (ii) MOLECULE TYPE: PEPTIDE (ix) FEATURE:
        (A) NAME/KEY: HUMAN iNOS (37-48)
        (B) LOCATION: CARBOXY TERMINAL WITH AMIDE
        (C) IDENTIFICATION METHOD: AMINO ACID ANALYSIS
        (D) OTHER INFORMATION:

(xi) SEQUENCE DESCRIPTION: SEQ ID NO: 49:

Ser Pro Val Thr Gln Asp Asp Leu Gln Tyr His Asn
                 5                   10

(2) INFORMATION FOR SEQ ID NO: 50:

(i) SEQUENCE CHARACTERISTICS:
        (A) LENGTH: 9
        (B) TYPE: AMINO ACID
        (D) TOPOLOGY: LINEAR (ii) MOLECULE TYPE: PEPTIDE (ix) FEATURE:
        (A) NAME/KEY: HUMAN iNOS (37-45)
        (B) LOCATION: CARBOXY TERMINAL WITH AMIDE
        (C) IDENTIFICATION METHOD: AMINO ACID ANALYSIS
        (D) OTHER INFORMATION:

(xi) SEQUENCE DESCRIPTION: SEQ ID NO: 50:

Ser Pro Val Thr Gln Asp Asp Leu Gln
                 5

(2) INFORMATION FOR SEQ ID NO: 51:

(i) SEQUENCE CHARACTERISTICS:
        (A) LENGTH: 6
        (B) TYPE: AMINO ACID
        (D) TOPOLOGY: LINEAR (ii) MOLECULE TYPE: PEPTIDE (ix) FEATURE:
        (A) NAME/KEY: HUMAN iNOS (37-42)
        (B) LOCATION: CARBOXY TERMINAL WITH AMIDE
        (C) IDENTIFICATION METHOD: AMINO ACID ANALYSIS
        (D) OTHER INFORMATION:

(xi) SEQUENCE DESCRIPTION: SEQ ID NO: 51:

Ser Pro Val Thr Gln Asp
                5

(2) INFORMATION FOR SEQ ID NO: 52:

(i) SEQUENCE CHARACTERISTICS:
        (A) LENGTH: 18
        (B) TYPE: AMINO ACID
        (D) TOPOLOGY: LINEAR (ii) MOLECULE TYPE: PEPTIDE (ix) FEATURE:
        (A) NAME/KEY: (F6) LOCUS HUMAN iNOS (781-798)
        (B) LOCATION: CARBOXY TERMINAL WITH AMIDE
        (C) IDENTIFICATION METHOD: AMINO ACID ANALYSIS
        (D) OTHER INFORMATION:

(xi) SEQUENCE DESCRIPTION: SEQ ID NO: 52:

Pro Ala Leu Val Gln Gly Ile Leu Glu Arg Val Val Asp
                    5                           10

Gly Pro Thr Pro His
                15

(2) INFORMATION FOR SEQ ID NO: 53:

(i) SEQUENCE CHARACTERISTICS:
        (A) LENGTH: 19
        (B) TYPE: AMINO ACID
        (D) TOPOLOGY: LINEAR (ii) MOLECULE TYPE: PEPTIDE (ix) FEATURE:
        (A) NAME/KEY: HUMAN eNOS (806-824)
        (B) LOCATION: CARBOXY TERMINAL WITH AMIDE
        (C) IDENTIFICATION METHOD: AMINO ACID ANALYSIS
        (D) OTHER INFORMATION:

(xi) SEQUENCE DESCRIPTION: SEQ ID NO: 53:

Pro Gly Leu Val Glu Ala Leu Leu Ser Arg Val Glu Asp
                    5                           10

Pro Pro Ala Pro Thr Glu
                    15

(2) INFORMATION FOR SEQ ID NO: 54:

(i) SEQUENCE CHARACTERISTICS:
        (A) LENGTH: 15
        (B) TYPE: AMINO ACID
        (D) TOPOLOGY: LINEAR (ii) MOLECULE TYPE: PEPTIDE (ix) FEATURE:
        (A) NAME/KEY: HUMAN iNOS (784-798)
        (B) LOCATION: CARBOXY TERMINAL WITH AMIDE
        (C) IDENTIFICATION METHOD: AMINO ACID ANALYSIS
        (D) OTHER INFORMATION:

(xi) SEQUENCE DESCRIPTION: SEQ ID NO: 54:

Val Gln Gly Ile Leu Glu Arg Val Val Asp Gly Pro Thr
                    5                           10

Pro His
    15

(2) INFORMATION FOR SEQ ID NO: 55:

(i) SEQUENCE CHARACTERISTICS:
        (A) LENGTH: 12
        (B) TYPE: AMINO ACID
        (D) TOPOLOGY: LINEAR (ii) MOLECULE TYPE: PEPTIDE (ix) FEATURE:
        (A) NAME/KEY: HUMAN iNOS (787-798)
        (B) LOCATION: CARBOXY TERMINAL WITH AMIDE
        (C) IDENTIFICATION METHOD: AMINO ACID ANALYSIS
        (D) OTHER INFORMATION:

(xi) SEQUENCE DESCRIPTION: SEQ ID NO: 55:

Ile Leu Glu Arg Val Val Asp Gly Pro Thr Pro His
                 5                   10

(2) INFORMATION FOR SEQ ID NO: 56:

(i) SEQUENCE CHARACTERISTICS:
        (A) LENGTH: 9
        (B) TYPE: AMINO ACID
        (D) TOPOLOGY: LINEAR (ii) MOLECULE TYPE: PEPTIDE (ix) FEATURE:
        (A) NAME/KEY: HUMAN iNOS (790-798)
        (B) LOCATION: CARBOXY TERMINAL WITH AMIDE
        (C) IDENTIFICATION METHOD: AMINO ACID ANALYSIS
        (D) OTHER INFORMATION:

(xi) SEQUENCE DESCRIPTION: SEQ ID NO: 56:

Arg Val Val Asp Gly Pro Thr Pro His
                 5

(2) INFORMATION FOR SEQ ID NO: 57:

(i) SEQUENCE CHARACTERISTICS:
        (A) LENGTH: 6
        (B) TYPE: AMINO ACID
        (D) TOPOLOGY: LINEAR (ii) MOLECULE TYPE: PEPTIDE (ix) FEATURE:
        (A) NAME/KEY: HUMAN iNOS (793-798)
        (B) LOCATION: CARBOXY TERMINAL WITH AMIDE
        (C) IDENTIFICATION METHOD: AMINO ACID ANALYSIS
        (D) OTHER INFORMATION:

(xi) SEQUENCE DESCRIPTION: SEQ ID NO: 57:

Asp Gly Pro Thr Pro His
                 5

(2) INFORMATION FOR SEQ ID NO: 58:

(i) SEQUENCE CHARACTERISTICS:
        (A) LENGTH: 14
        (B) TYPE: AMINO ACID
        (D) TOPOLOGY: LINEAR (ii) MOLECULE TYPE: PEPTIDE (ix) FEATURE:
        (A) NAME/KEY: HUMAN iNOS (781-794)
        (B) LOCATION: CARBOXY TERMINAL WITH AMIDE
        (C) IDENTIFICATION METHOD: AMINO ACID ANALYSIS
        (D) OTHER INFORMATION:

(xi) SEQUENCE DESCRIPTION: SEQ ID NO: 58:

```
Pro  Ala  Leu  Val  Gln  Gly  Ile  Leu  Glu  Arg  Val  Val  Asp
                    5                        10
Gly
```

(2) INFORMATION FOR SEQ ID NO: 59:

(i) SEQUENCE CHARACTERISTICS:
        (A) LENGTH: 12
        (B) TYPE: AMINO ACID
        (D) TOPOLOGY: LINEAR (ii) MOLECULE TYPE: PEPTIDE (ix) FEATURE:
        (A) NAME/KEY: HUMAN iNOS (781-792)
        (B) LOCATION: CARBOXY TERMINAL WITH AMIDE
        (C) IDENTIFICATION METHOD: AMINO ACID ANALYSIS
        (D) OTHER INFORMATION:

(xi) SEQUENCE DESCRIPTION: SEQ ID NO: 59:

```
Pro  Ala  Leu  Val  Gln  Gly  Ile  Leu  Glu  Arg  Val  Val
                    5                        10
```

(2) INFORMATION FOR SEQ ID NO: 60:

(i) SEQUENCE CHARACTERISTICS:
        (A) LENGTH: 9
        (B) TYPE: AMINO ACID
        (D) TOPOLOGY: LINEAR (ii) MOLECULE TYPE: PEPTIDE (ix) FEATURE:
        (A) NAME/KEY: HUMAN iNOS (781-789)
        (B) LOCATION: CARBOXY TERMINAL WITH AMIDE
        (C) IDENTIFICATION METHOD: AMINO ACID ANALYSIS
        (D) OTHER INFORMATION:

(xi) SEQUENCE DESCRIPTION: SEQ ID NO: 60:

```
Pro  Ala  Leu  Val  Gln  Gly  Ile  Leu  Glu
                    5
```

(2) INFORMATION FOR SEQ ID NO: 61:

(i) SEQUENCE CHARACTERISTICS:
        (A) LENGTH: 6
        (B) TYPE: AMINO ACID
        (D) TOPOLOGY: LINEAR (ii) MOLECULE TYPE: PEPTIDE (ix) FEATURE:
        (A) NAME/KEY: HUMAN iNOS (781-786)
        (B) LOCATION: CARBOXY TERMINAL WITH AMIDE
        (C) IDENTIFICATION METHOD: AMINO ACID ANALYSIS
        (D) OTHER INFORMATION:

(xi) SEQUENCE DESCRIPTION: SEQ ID NO: 61:

```
Pro  Ala  Leu  Val  Gln  Gly
                    5
```

(2) INFORMATION FOR SEQ ID NO: 62:

(i) SEQUENCE CHARACTERISTICS:
        (A) LENGTH: 18
        (B) TYPE: AMINO ACID
        (D) TOPOLOGY: LINEAR (ii) MOLECULE TYPE: PEPTIDE (ix) FEATURE:
        (A) NAME/KEY: (G11) LOCUS HUMAN iNOS (985-1002)
        (B) LOCATION: CARBOXY TERMINAL WITH AMIDE
        (C) IDENTIFICATION METHOD: AMINO ACID ANALYSIS
        (D) OTHER INFORMATION:

(xi) SEQUENCE DESCRIPTION: SEQ ID NO: 62:

Gly  Ile  Val  Pro  Phe  Arg  Ser  Phe  Trp  Gln  Gln  Arg  Leu
                         5                        10

His  Asp  Ser  Gln  His
         15

(2) INFORMATION FOR SEQ ID NO: 63:

(i) SEQUENCE CHARACTERISTICS:
        (A) LENGTH: 18
        (B) TYPE: AMINO ACID
        (D) TOPOLOGY: LINEAR (ii) MOLECULE TYPE: PEPTIDE (ix) FEATURE:
        (A) NAME/KEY: HUMAN nNOS (1256-1273)
        (B) LOCATION: CARBOXY TERMINAL WITH AMIDE
        (C) IDENTIFICATION METHOD: AMINO ACID ANALYSIS
        (D) OTHER INFORMATION:

(xi) SEQUENCE DESCRIPTION: SEQ ID NO: 63:

Gly  Ile  Ala  Pro  Phe  Arg  Ser  Phe  Trp  Gln  Gln  Arg  Gln
                         5                        10

Phe  Asp  Ile  Gln  His
         15

(2) INFORMATION FOR SEQ ID NO: 64:

(i) SEQUENCE CHARACTERISTICS:
        (A) LENGTH: 15
        (B) TYPE: AMINO ACID
        (D) TOPOLOGY: LINEAR (ii) MOLECULE TYPE: PEPTIDE (ix) FEATURE:
        (A) NAME/KEY: HUMAN eNOS (1017-1031)
        (B) LOCATION: CARBOXY TERMINAL WITH AMIDE
        (C) IDENTIFICATION METHOD: AMINO ACID ANALYSIS
        (D) OTHER INFORMATION:

(xi) SEQUENCE DESCRIPTION: SEQ ID NO: 64:

Gly  Ile  Ala  Pro  Phe  Arg  Gly  Phe  Trp  Gln  Glu  Arg  Leu
                         5                        10

His  Asp
    15

(2) INFORMATION FOR SEQ ID NO: 65:

(i) SEQUENCE CHARACTERISTICS:
        (A) LENGTH: 15
        (B) TYPE: AMINO ACID
        (D) TOPOLOGY: LINEAR (ii) MOLECULE TYPE: PEPTIDE (ix) FEATURE:
        (A) NAME/KEY: HUMAN iNOS (988-1002)
        (B) LOCATION: CARBOXY TERMINAL WITH AMIDE
        (C) IDENTIFICATION METHOD: AMINO ACID ANALYSIS
        (D) OTHER INFORMATION:

(xi) SEQUENCE DESCRIPTION: SEQ ID NO: 65:

```
Pro  Phe  Arg  Ser  Phe  Trp  Gln  Gln  Arg  Leu  His  Asp  Ser
               5                        10

Gln  His
     15

(2) INFORMATION FOR SEQ ID NO: 66:

(i) SEQUENCE CHARACTERISTICS:
        (A) LENGTH: 12
        (B) TYPE: AMINO ACID
        (D) TOPOLOGY: LINEAR (ii) MOLECULE TYPE: PEPTIDE (ix) FEATURE:
        (A) NAME/KEY: HUMAN iNOS (991-1002)
        (B) LOCATION: CARBOXY TERMINAL WITH AMIDE
        (C) IDENTIFICATION METHOD: AMINO ACID ANALYSIS
        (D) OTHER INFORMATION:

(xi) SEQUENCE DESCRIPTION: SEQ ID NO: 66:

Ser  Phe  Trp  Gln  Gln  Arg  Leu  His  Asp  Ser  Gln  His
               5                        10

(2) INFORMATION FOR SEQ ID NO: 67:

(i) SEQUENCE CHARACTERISTICS:
        (A) LENGTH: 9
        (B) TYPE: AMINO ACID
        (D) TOPOLOGY: LINEAR (ii) MOLECULE TYPE: PEPTIDE (ix) FEATURE:
        (A) NAME/KEY: HUMAN iNOS (994-1002)
        (B) LOCATION: CARBOXY TERMINAL WITH AMIDE
        (C) IDENTIFICATION METHOD: AMINO ACID ANALYSIS
        (D) OTHER INFORMATION:

(xi) SEQUENCE DESCRIPTION: SEQ ID NO: 67:

Gln  Gln  Arg  Leu  His  Asp  Ser  Gln  His
               5

(2) INFORMATION FOR SEQ ID NO: 68:

(i) SEQUENCE CHARACTERISTICS:
        (A) LENGTH: 5
        (B) TYPE: AMINO ACID
        (D) TOPOLOGY: LINEAR (ii) MOLECULE TYPE: PEPTIDE (ix) FEATURE:
        (A) NAME/KEY: HUMAN iNOS (997-1002)
        (B) LOCATION: CARBOXY TERMINAL WITH AMIDE
        (C) IDENTIFICATION METHOD: AMINO ACID ANALYSIS
        (D) OTHER INFORMATION:

(xi) SEQUENCE DESCRIPTION: SEQ ID NO: 68:

His  Asp  Ser  Gln  His
               5

(2) INFORMATION FOR SEQ ID NO: 69:

(i) SEQUENCE CHARACTERISTICS:
        (A) LENGTH: 15
        (B) TYPE: AMINO ACID
        (D) TOPOLOGY: LINEAR (ii) MOLECULE TYPE: PEPTIDE
```

(ix) FEATURE:
              (A) NAME/KEY: HUMAN iNOS (985-998)
              (B) LOCATION: CARBOXY TERMINAL WITH AMIDE
              (C) IDENTIFICATION METHOD: AMINO ACID ANALYSIS
              (D) OTHER INFORMATION:

(xi) SEQUENCE DESCRIPTION: SEQ ID NO: 69:

Gly   Ile   Val   Pro   Phe   Arg   Ser   Phe   Trp   Gln   Gln   Arg   Leu
                         5                           10

His   Asp
      15

(2) INFORMATION FOR SEQ ID NO: 70:

(i) SEQUENCE CHARACTERISTICS:
              (A) LENGTH: 12
              (B) TYPE: AMINO ACID
              (D) TOPOLOGY: LINEAR (ii) MOLECULE TYPE: PEPTIDE (ix) FEATURE:
              (A) NAME/KEY: HUMAN iNOS (985-996)
              (B) LOCATION: CARBOXY TERMINAL WITH AMIDE
              (C) IDENTIFICATION METHOD: AMINO ACID ANALYSIS
              (D) OTHER INFORMATION:

(xi) SEQUENCE DESCRIPTION: SEQ ID NO: 70:

Gly   Ile   Val   Pro   Phe   Arg   Ser   Phe   Trp   Gln   Gln   Arg
                         5                           10

(2) INFORMATION FOR SEQ ID NO: 71:

(i) SEQUENCE CHARACTERISTICS:
              (A) LENGTH: 9
              (B) TYPE: AMINO ACID
              (D) TOPOLOGY: LINEAR (ii) MOLECULE TYPE: PEPTIDE (ix) FEATURE:
              (A) NAME/KEY: HUMAN iNOS (985-993)
              (B) LOCATION: CARBOXY TERMINAL WITH AMIDE
              (C) IDENTIFICATION METHOD: AMINO ACID ANALYSIS
              (D) OTHER INFORMATION:

(xi) SEQUENCE DESCRIPTION: SEQ ID NO: 71:

Gly   Ile   Val   Pro   Phe   Arg   Ser   Phe   Trp
                         5

(2) INFORMATION FOR SEQ ID NO: 72:

(i) SEQUENCE CHARACTERISTICS:
              (A) LENGTH: 6
              (B) TYPE: AMINO ACID
              (D) TOPOLOGY: LINEAR (ii) MOLECULE TYPE: PEPTIDE (ix) FEATURE:
              (A) NAME/KEY: HUMAN iNOS (985-990)
              (B) LOCATION: CARBOXY TERMINAL WITH AMIDE
              (C) IDENTIFICATION METHOD: AMINO ACID ANALYSIS
              (D) OTHER INFORMATION:

(xi) SEQUENCE DESCRIPTION: SEQ ID NO: 72:

Gly   Ile   Val   Pro   Phe   Arg
                         5

(2) INFORMATION FOR SEQ ID NO: 73:

(i) SEQUENCE CHARACTERISTICS:
        (A) LENGTH: 18
        (B) TYPE: AMINO ACID
        (D) TOPOLOGY: LINEAR (ii) MOLECULE TYPE: PEPTIDE (ix) FEATURE:
        (A) NAME/KEY: (H1) LOCUS HUMAN iNOS (1009-1026)
        (B) LOCATION: CARBOXY TERMINAL WITH AMIDE
        (C) IDENTIFICATION METHOD: AMINO ACID ANALYSIS
        (D) OTHER INFORMATION:

(xi) SEQUENCE DESCRIPTION: SEQ ID NO: 73:

Arg  Met  Thr  Leu  Val  Phe  Gly  Ser  Arg  Arg  Pro  Asp  Glu
                    5                        10

Asp  His  Ile  Tyr  Gln
     15

(2) INFORMATION FOR SEQ ID NO: 74:

(i) SEQUENCE CHARACTERISTICS:
        (A) LENGTH: 17
        (B) TYPE: AMINO ACID
        (D) TOPOLOGY: LINEAR (ii) MOLECULE TYPE: PEPTIDE (ix) FEATURE:
        (A) NAME/KEY: HUMAN eNOS (1041-1057)
        (B) LOCATION: CARBOXY TERMINAL WITH AMIDE
        (C) IDENTIFICATION METHOD: AMINO ACID ANALYSIS
        (D) OTHER INFORMATION:

(xi) SEQUENCE DESCRIPTION: SEQ ID NO: 74:

Met  Thr  Leu  Val  Phe  Gly  Ser  Arg  Ser  Ser  Gln  Leu  Asp
                    5                        10

His  Leu  Tyr  Arg
     15

(2) INFORMATION FOR SEQ ID NO: 75:

(i) SEQUENCE CHARACTERISTICS:
        (A) LENGTH: 17
        (B) TYPE: AMINO ACID
        (D) TOPOLOGY: LINEAR (ii) MOLECULE TYPE: PEPTIDE (ix) FEATURE:
        (A) NAME/KEY: HUMAN nNOS (1281-1297)
        (B) LOCATION: CARBOXY TERMINAL WITH AMIDE
        (C) IDENTIFICATION METHOD: AMINO ACID ANALYSIS
        (D) OTHER INFORMATION:

(xi) SEQUENCE DESCRIPTION: SEQ ID NO: 75:

Met  Val  Leu  Val  Phe  Gly  Ser  Arg  Gln  Ser  Lys  Ile  Asp
                    5                        10

His  Ile  Tyr  Arg
     15

(2) INFORMATION FOR SEQ ID NO: 76:

(i) SEQUENCE CHARACTERISTICS:
        (A) LENGTH: 15
        (B) TYPE: AMINO ACID
        (D) TOPOLOGY: LINEAR (ii) MOLECULE TYPE: PEPTIDE (ix) FEATURE:
            (A) NAME/KEY: HUMAN iNOS (1012-1026)
            (B) LOCATION: CARBOXY TERMINAL WITH AMIDE
            (C) IDENTIFICATION METHOD: AMINO ACID ANALYSIS
            (D) OTHER INFORMATION:

(xi) SEQUENCE DESCRIPTION: SEQ ID NO: 76:

Leu  Val  Phe  Gly  Ser  Arg  Arg  Pro  Asp  Glu  Asp  His  Ile
                    5                        10

Tyr  Gln
     15

(2) INFORMATION FOR SEQ ID NO: 77:

(i) SEQUENCE CHARACTERISTICS:
            (A) LENGTH: 12
            (B) TYPE: AMINO ACID
            (D) TOPOLOGY: LINEAR (ii) MOLECULE TYPE: PEPTIDE (ix) FEATURE:
            (A) NAME/KEY: HUMAN iNOS (1015-1026)
            (B) LOCATION: CARBOXY TERMINAL WITH AMIDE
            (C) IDENTIFICATION METHOD: AMINO ACID ANALYSIS
            (D) OTHER INFORMATION:

(xi) SEQUENCE DESCRIPTION: SEQ ID NO: 77:

Gly  Ser  Arg  Arg  Pro  Asp  Glu  Asp  His  Ile  Tyr  Gln
                    5                        10

(2) INFORMATION FOR SEQ ID NO: 78:

(i) SEQUENCE CHARACTERISTICS:
            (A) LENGTH: 9
            (B) TYPE: AMINO ACID
            (D) TOPOLOGY: LINEAR (ii) MOLECULE TYPE: PEPTIDE (ix) FEATURE:
            (A) NAME/KEY: HUMAN iNOS (1018-1026)
            (B) LOCATION: CARBOXY TERMINAL WITH AMIDE
            (C) IDENTIFICATION METHOD: AMINO ACID ANALYSIS
            (D) OTHER INFORMATION:

(xi) SEQUENCE DESCRIPTION: SEQ ID NO: 78:

Arg  Pro  Asp  Glu  Asp  His  Ile  Tyr  Gln
                    5

(2) INFORMATION FOR SEQ ID NO: 79:

(i) SEQUENCE CHARACTERISTICS:
            (A) LENGTH: 6
            (B) TYPE: AMINO ACID
            (D) TOPOLOGY: LINEAR (ii) MOLECULE TYPE: PEPTIDE (ix) FEATURE:
            (A) NAME/KEY: HUMAN iNOS (1021-1026)
            (B) LOCATION: CARBOXY TERMINAL WITH AMIDE
            (C) IDENTIFICATION METHOD: AMINO ACID ANALYSIS
            (D) OTHER INFORMATION:

(xi) SEQUENCE DESCRIPTION: SEQ ID NO: 79:

Glu  Asp  His  Ile  Tyr  Gln
                    5

(2) INFORMATION FOR SEQ ID NO: 80:

(i) SEQUENCE CHARACTERISTICS:
        (A) LENGTH: 15
        (B) TYPE: AMINO ACID
        (D) TOPOLOGY: LINEAR (ii) MOLECULE TYPE: PEPTIDE (ix) FEATURE:
        (A) NAME/KEY: HUMAN iNOS (1009-1023)
        (B) LOCATION: CARBOXY TERMINAL WITH AMIDE
        (C) IDENTIFICATION METHOD: AMINO ACID ANALYSIS
        (D) OTHER INFORMATION:

(xi) SEQUENCE DESCRIPTION: SEQ ID NO: 80:

Arg Met Thr Leu Val Phe Gly Ser Arg Arg Pro Asp Glu
                5                    10

Asp His
    15

(2) INFORMATION FOR SEQ ID NO: 81:

(i) SEQUENCE CHARACTERISTICS:
        (A) LENGTH: 11
        (B) TYPE: AMINO ACID
        (D) TOPOLOGY: LINEAR (ii) MOLECULE TYPE: PEPTIDE (ix) FEATURE:
        (A) NAME/KEY: HUMAN iNOS (1009-1020)
        (B) LOCATION: CARBOXY TERMINAL WITH AMIDE
        (C) IDENTIFICATION METHOD: AMINO ACID ANALYSIS
        (D) OTHER INFORMATION:

(xi) SEQUENCE DESCRIPTION: SEQ ID NO: 81:

Arg Met Thr Leu Val Phe Gly Ser Arg Arg Pro
                5                    10

(2) INFORMATION FOR SEQ ID NO: 82:

(i) SEQUENCE CHARACTERISTICS:
        (A) LENGTH: 9
        (B) TYPE: AMINO ACID
        (D) TOPOLOGY: LINEAR (ii) MOLECULE TYPE: PEPTIDE (ix) FEATURE:
        (A) NAME/KEY: HUMAN iNOS (1009-1017)
        (B) LOCATION: CARBOXY TERMINAL WITH AMIDE
        (C) IDENTIFICATION METHOD: AMINO ACID ANALYSIS
        (D) OTHER INFORMATION:

(xi) SEQUENCE DESCRIPTION: SEQ ID NO: 82:

Arg Met Thr Leu Val Phe Gly Ser Arg
                5

(2) INFORMATION FOR SEQ ID NO: 83:

(i) SEQUENCE CHARACTERISTICS:
        (A) LENGTH: 6
        (B) TYPE: AMINO ACID
        (D) TOPOLOGY: LINEAR (ii) MOLECULE TYPE: PEPTIDE (ix) FEATURE:
        (A) NAME/KEY: HUMAN iNOS (1009-1014)
        (B) LOCATION: CARBOXY TERMINAL WITH AMIDE

```
            (C) IDENTIFICATION METHOD: AMINO ACID ANALYSIS
            (D) OTHER INFORMATION:

(xi) SEQUENCE DESCRIPTION: SEQ ID NO: 83:

Arg  Met  Thr  Leu  Val  Phe
                         5

(2) INFORMATION FOR SEQ ID NO: 84:

(i) SEQUENCE CHARACTERISTICS:
            (A) LENGTH: 12
            (B) TYPE: AMINO ACID
            (D) TOPOLOGY: LINEAR (ii) MOLECULE TYPE: PEPTIDE (ix) FEATURE:
            (A) NAME/KEY: TRUNCATED HUMAN iNOS (40-54)
            (B) LOCATION: CARBOXY TERMINAL WITH AMIDE
            (C) IDENTIFICATION METHOD: AMINO ACID ANALYSIS
            (D) OTHER INFORMATION:

(xi) SEQUENCE DESCRIPTION: SEQ ID NO: 84:

Thr  Gln  Asp  Asp  Leu  Gln  Tyr  His  Asn  Leu  Ser  Lys
                    5                          10

(2) INFORMATION FOR SEQ ID NO: 85:

(i) SEQUENCE CHARACTERISTICS:
            (A) LENGTH: 9
            (B) TYPE: AMINO ACID
            (D) TOPOLOGY: LINEAR (ii) MOLECULE TYPE: PEPTIDE (ix) FEATURE:
            (A) NAME/KEY: TRUNCATED HUMAN iNOS (784-798)
            (B) LOCATION: CARBOXY TERMINAL WITH AMIDE
            (C) IDENTIFICATION METHOD: AMINO ACID ANALYSIS
            (D) OTHER INFORMATION:

(xi) SEQUENCE DESCRIPTION: SEQ ID NO: 85:

Val  Gln  Gly  Ile  Leu  Glu  Arg  Val  Val
                    5
```